(12) United States Patent
Honda et al.

(10) Patent No.: US 12,629,395 B2
(45) Date of Patent: May 19, 2026

(54) **COMPOSITION FOR INHIBITING TRYPSIN ACTIVITY CONTAINING AS ACTIVE INGREDIENT BACTERIUM BELONGING TO GENUS *PARAPREVOTELLA***

(71) Applicant: RIKEN, Wako (JP)

(72) Inventors: Kenya Honda, Wako (JP); Seiko Narushima, Wako (JP); Eiichiro Watanabe, Wako (JP); Osamu Ohara, Wako (JP); Yusuke Kawashima, Wako (JP); Youxian Li, Wako (JP)

(73) Assignee: RIKEN, Saitama (JP)

( * ) Notice: Subject to any disclaimer, the term of this patent is extended or adjusted under 35 U.S.C. 154(b) by 473 days.

(21) Appl. No.: 18/184,254

(22) Filed: Mar. 15, 2023

(65) Prior Publication Data

US 2023/0263839 A1    Aug. 24, 2023

Related U.S. Application Data

(63) Continuation of application No. 17/274,610, filed as application No. PCT/JP2019/035574 on Sep. 10, 2019, now abandoned.

(60) Provisional application No. 62/794,145, filed on Jan. 18, 2019, provisional application No. 62/728,908, filed on Sep. 10, 2018.

(51) Int. Cl.
    *A61K 35/74*             (2015.01)

(52) U.S. Cl.
    CPC .................................... *A61K 35/74* (2013.01)

(58) Field of Classification Search
    CPC .................................. A61K 35/74; A61P 1/00
    See application file for complete search history.

(56) References Cited

U.S. PATENT DOCUMENTS

2018/0110800 A1    4/2018    Dutta

FOREIGN PATENT DOCUMENTS

| JP | 2015-537042 A | 12/2015 |
| JP | 2018-502551 A | 2/2018 |
| WO | 2015/003001 A1 | 1/2015 |
| WO | 2015/051323 A1 | 4/2015 |
| WO | 2018/117263 A1 | 6/2018 |

OTHER PUBLICATIONS

"Hit details for EM_STD:HQ766248 Uncultured organism clone ELU0059-T397-S-NIPCRAMgANa_000409 small subunit ribosomal RNA", Jan. 1, 2012, pp. 1, XP055919100, Retrieved from the Internet: URL :http ://ibis.internal.epo.org/exam/dbfetch.jsp?id=EM_STD%3AHQ766248 (1 page total).

Eckburg et al., "Diversity of the Human Intestinal Microbial Flora", Science, vol. 308, Jun. 10, pp. 1635-1638, 2005 (5 pages total).

Extended European Search Report dated May 17, 2022 from the European Patent Office in EP Application No. 19858845.1.

Francoise Ramare et al., "Inactivation of Tryptic Activity by a Human-Derived Strain of Bacteroides distasonis in the Large Intestines of Gnotobiotic Rats and Mice", Applied and Environmental Microbiology, Apr. 1996, vol. 62, No. 4, pp. 1434-1436 (3 pages total).

International Preliminary Report of Patentability with a Translation of the Written Opinion of the International Searching Authority dated Mar. 9, 2021 in Application No. PCT/JP2019/035574.

J.P. Van De Merwe et al., "Levels of Trypsin and a-Chymotrypsin in Feces from Patients with Crohn's Disease", Digestion, 1982, vol. 24, pp. 1-4 (4 pages total).

Jeffrey J. Bunker et al., "Innate and adaptive humoral responses coat distinct commensal bacteria with immunoglobulin A", Immunity, Sep. 15, 2016, 43(3):541-553; pp. 1-25 (25 pages total).

Joseph D. Planer et al., "Development of the gut microbiota and mucosal IgA responses in twins and gnotobiotic mice", Nature, vol. 534, No. (7606):263-266, Nov. 25, 2016, pp. 1-26 (26 pages total).

Koji Atarashi et al., "Ectopic colonization of oral bacteria in the intestine drives TH1 cell induction and inflammation", Science, Oct. 20, 2017, vol. 358 (6361), pp. 359-365 (7 pages total).

Koji Atarashi et al., "Th17 Cell Induction by Adhesion of Microbes to Intestinal Epithelial Cells", Cell, Oct. 8, 2015, vol. 163, issue 2, pp. 367-380 (38 pages total).

Koji Atarashi et al., "Treg induction by a rationally selected mixture of Clostridia strains from the human microbiota", Nature, Aug. 8, 2013, vol. 500, pp. 232-236 (7 pages total).

M. Morotomi et al., "Paraprevotella clara gene for 16S ribosomal RNA, partial sequence", Genbank AB331896.1, https://www.ncbi.nlm.nih.gov/nuccore/AB331896.1/, retrieved Dec. 4, 2019.

M. Sakamoto et al., "Paraprevotella clara gene for 16S ribosomal RNA, partial sequence, strain: JCM 14859", Genbank ab547651.1, https://www.ncbi.nlm.nih.gov/nuccore/AB547651, retrieved Dec. 4, 2019.

Mimtsuo Sakamoto et al., "Usefulness of the hsp60 gene for the identification and classification of Gram-negative anaerobic rods", Journal of Medical Microbiology, 2010, vol. 59, pp. 1293-1302 (10 pages total).

Morotomi et al., "*Paraprevotella clara* gen. nov., sp. nov. and *Paraprevotella xylaniphila* sp. nov., members of the family 1 Prevotellaceae isolated from human faeces", International Journal of Systematic and Evolutionary Microbiology, vol. 59, pp. 1895-1900, 2009 (6 pages total).

Noah W. Palm et al., "Immunoglobulin A Coating Identifies Colitogenic Bacteria in Inflammatory Bowel Disease", Cell, Aug. 28, 2014, vol. 158, issue 5, pp. 1000-1010 (11 pages total).

Ramare et al., "Inactivation of Tryptic Activity by a Human-Derived Strain of Bacteroides distasonis in the Large Intestines of Gnotobiotic Rats and Mice", Applied and Environmental Microbiology, vol. 62, No. 4, pp. 1434-1436, Apr. 1996 (3 pages total).

(Continued)

*Primary Examiner* — Kade Ariani

(74) *Attorney, Agent, or Firm* — Sughrue Mion, PLLC

(57) ABSTRACT

A composition for suppressing trypsin activity is disclosed. The composition contains a bacterium belonging to a genus *Paraprevotella* as an active ingredient.

7 Claims, 15 Drawing Sheets

Specification includes a Sequence Listing.

(56)     References Cited

OTHER PUBLICATIONS

Shimpei Kawamoto et al., "Foxp3+ T Cells Regulate Immunoglobulin A Selection and Facilitate Diversification of Bacterial Species Responsible for Immune Homeostasis" Immunity, Jul. 17, 2014, vol. 41, issue 1, pp. 152-165 (14 pages total).

Tore Midtvedt et al., "Increase of Faecal Tryptic Activity Relates to Changes in the Intestinal Microbiome: Analysis of Crohn's Disease with a Multidisciplinary Platform", Plos One, Jun. 2013, vol. 8, issue 6, pp. 1-9 (9 pages total).

Li et al., Frontiers in Microbiology, Mar. 2017, vol. 8, Article 484, p. 1-11.

Konstantinidis et al,, PNAS, 2005, vol. 102, No. 7, p. 2567-2572.

Riken BRC Microbe Division website for microorganism culture distribution, https://jcm.brc.riken.jp/en/ordering_e, last visited Mar. 9, 2023.

SEQUENCE LISTING

```
Sequence total quantity: 13
SEQ ID NO: 1          moltype = DNA  length = 1359
FEATURE               Location/Qualifiers
misc_feature          1..1359
                      note = Paraprevotella clara 1C4
misc_difference       307..308
                      note = n is a, c, g, or t
source                1..1359
                      mol_type = other DNA
                      organism = Paraprevotella clara
SEQUENCE: 1
cagctttgct gagtttgatg gcgaccggcg cacgggtgag taacgcgtat ccaacctgcc   60
ctttactccg ggatagtctc ctgaaaggga gtttaatacc ggatgtgttt gttttccgc   120
atgggagcga caaataaaga ttaattggta aaggatgggg atgcgtccca ttagcttgtt   180
ggcggggtaa cggcccacca aggcgacgat gggtaggggt tctgagagga aggtcccca   240
```

```
cattggaact gagacacggt ccaaactcct acgggaggca gcagtgagga atattggtca    300
atgggcnnga gcctgaacca gccaagtagc gtgaaggacg acggccctac gggttgtaaa    360
cttctttat aagggaataa agttcgccac gcgtggtgtt ttgtatgtac cttatgaata    420
agcatcggct aattccgtgc cagcagccgc ggtaatacgg aagatgcgag cgttatccgg    480
atttattggg tttaaaggga gcgtaggcgg gcttttaagt cagcggtcaa atgccacgc    540
tcaaccgtgg ccagccgttg aaactgtaag ccttgagtct gcacaggca catggaattc    600
gtggtgtagc ggtgaaatgc ttagatatca cgaagaactc cgatcgcgaa ggcattgtgc    660
cggggcagca ctgacgctga ggctcgaaag tgcgggtatc aaacaggatt agataccctg    720
gtagtccgca cggtaaacga tgaatgctcg ctatgggcga tatattgtcc gtggccaagc    780
gaaagcgtta agcattccac ctggggagta cgccggcaac ggtgaaactc aaaggaattg    840
acggggggccc gcacaagcgg aggaacatgt ggtttaattc gatgatacgc gaggaacctt    900
acccgggcctt gaattgcagg tgcatgagtc agagacggct ctttccttcg ggactcctgt    960
gaaggtgctg catggttgtc gtcagctcgt gccgtgaggt gtcggcttaa gtgccataac   1020
gagcgcaacc cttctcccca gttgccatcg ggtaatgccg ggccctctgg ggacactgcc   1080
atcgtaagat gcgaggaagg tggggatgac gtcaaatcag cacggcccctt acgtccgggg   1140
ctacacacgt gttacaatgg ggggtacaga gggccgctgt ccggtgacgg tcggccaatc   1200
cctaaaaccc ctctcagttc ggactggagt ctgcaacccg actccacgaa gctggattcg   1260
ctagtaatcg cgcatcagcc atggcgcggt gaatacgttc ccgggccttg tacacaccgc   1320
ccgtcaagcc atgaaagccg ggggtgcctg aagtccgtg                          1359

SEQ ID NO: 2              moltype = DNA  length = 1483
FEATURE                   Location/Qualifiers
misc_feature             1..1483
                          note = Paraprevotella clara JCM14859T
source                    1..1483
                          mol_type = other DNA
                          organism = Paraprevotella clara
SEQUENCE: 2
gatgaacgct agctacaggc ttaacacatg caagtcgagg ggcagcatgr rcycagcttt     60
gctgggtttg atggcgaccg gcgcacgggt gagtaacgcg tatccaacct gccctttact    120
ccgggatagt ctcctgaaag ggagtttaat accggatgtg tttgtctttc cgcatgggag    180
cgacaaataa agattgattg gtaaaggatg gggatgcgtc ccattagctr gttggcgggg    240
taacggccca ccaaggcrac gatgggtagg ggttctgaga ggaaggtccc ccacattgga    300
actgagacac ggtccaaact cctacgggag gcagcagtga ggaatattgg tcaatgggcg    360
agagcctgaa ccagccaagt agcgtgaagg acgacgaccc tacgggttgt aaacttcttt    420
tataagggaa taaagttcgc cacgcgtggt gttttgtatg taccttatga ataagcatcg    480
gctaattccg tgccagcagc cgcggtaata cggaagatgc gagcgttatc cggatttatt    540
gggtttaaag ggagcgtagg cgggctttta agtcagcggt caaatgtcac ggctcaaccg    600
tggccagcag ttgaaactgt aagccttgag tctgcacagg gcacatggtt tcgtggtgt    660
agcggtgaaa tgcttagata tcacgaagaa ctccgatcgc gaaggcattg tgccggggca    720
gcactgacgc tgaggctcga agtgcgggt atcaaacagg attagatacc ctggtagtcc    780
gcacggtaaa cgatgaatgc tcgctatggg cgatayawtg tccgtggcca agcgaaagcg    840
ttaagcattc cacctgggga gtacgccggc aacggtgaaa ctcaaaggaa ttgacgggggc    900
cccgcacaag cggaggaaca tgtggtttaa ttcgatgata cgcgaggaac cttacccggg    960
cttgaattgc aggtgcatga gtcagagatg attctttcct tcgggactcc tgtgaaggtg   1020
ctgcatggtt gtcgtcagct cgtgccgtga ggtgtcggct taagtgccat aacgagcgca   1080
accccttctcc ccagttgcca tcgggtaatg ccgggcccctc tgggggacact gccatcgtaa   1140
gatgcgagga aggtgggggat gacgtcaaat cagcacggcc cttacgtccg gggctacaca   1200
cgtgttacaa tggggggggtac agagggccgc tgtccggtga cggttggcca atccctaaaa   1260
ccctctcag ttcggactgg agtctgcaac ccgactccac gaagctggat cgctagtaa   1320
tcgcgcatca gccatggcgc ggtgaatacg ttcccgtggc ttgtacacac cgcccgtcaa   1380
gccatgaaag ccgggggtgc ctgaagtccg tgaccgcgag ggtcggccta gggtaaaact   1440
ggtgattggg gctaagtcgt aacaaggtag ccgtaccgga agg                     1483

SEQ ID NO: 3              moltype = DNA  length = 1481
FEATURE                   Location/Qualifiers
misc_feature             1..1481
                          note = Paraprevotella xylaniphila JCM14860T
source                    1..1481
                          mol_type = other DNA
                          organism = Paraprevotella xylaniphila
SEQUENCE: 3
gatgaacgct agctacaggc ttaacacatg caagtcgagg ggcagcatga acttagcttg     60
ctaagtttga tggcgaccgg cgcacggggt agtaacgcgt atccaacctg ccctttacg     120
ggggatagcc ttctgaaagg aagtttaata cccgatgaat tcgtttagtc gcatggcttg    180
atgaataaag atttatcagt aaaggatggg gatgcgtccc attagcttgt tggcggggta    240
acggcccacc aaggcgacga tgggtagggg ttctgagagg aagtcccccc acattggaac    300
tgagacacgg tccaaactcc tacgggaggc agcagtgagg aatattggtc aatgggcgcg    360
agcctgaacc agccaagtag cgtgaggac gacggcccta cgggttgtaa actccttta    420
taagggggata aagttggcca tgtatggcca tttgcaggta ccttatgaat aagcatcggc    480
taattccgtg ccagcagccg cggtaatacg gaagatgcga gcgttatccg gatttattgg    540
gtttaaaggg agcgtaggcg ggcagtcaag tcagcggtca aatggcgcgg ctcaaccgcg    600
ttcccgccgtt gaaactggca gccttgagta tgcacacggg acatggaatt cgtggtgtag    660
cggtgaaatg cttagatatc acgaggaact ccgatcgcga aggcattgta cgggggcatt    720
actgacgctg aggctcgaag tgcgggtat caaacaggat tagatacct ggtagtccgc    780
acagtaaacg atgaatgccc gctgtcgcgc acatagtgtc ggcggccaag cgaaagcgtt    840
aagcattcca cctggggagt acgccggcaa cggtgaaact caaaggaatt gacgggggc    900
cgcacaagcg aggaacatg tggtttaatt cgatgatacg cgaggaacct tacccgggct    960
tgaatcgcag gtgcatgggc cggagacggc cctttccttc gggactcctg cgaaggtgct   1020
```

-continued

```
gcatggttgt cgtcagctcg tgccgtgagg tgtcggctta agtgccataa cgagcgcaac   1080
cccctcccc  agttgccatc gggtaatgcc gggcactttg gggacactgc caccgcaagg   1140
tgcgaggaag gtggggatga cgtcaaatca gcacggccct tacgtccggg gcgacacacg   1200
tgttacaatg gggggtacag agggccgctg cccggtgacg gttggccaat ccctaaagcc   1260
cctctcagtt cggactggag tctgcaaccc gactccacga agctggattc gctagtaatc   1320
gcgcatcagc catggcgcgg tgaatacgtt cccgggcctt gtacacaccg cccgtcaagc   1380
catgaaagcc ggggggtgcct gaagtccgtg accgcgaggg tcggcctagg gtaaaaccgg   1440
tgattggggc taagtcgtaa caaggtagcc gtaccggaag g                       1481
```

SEQ ID NO: 4                moltype = DNA   length = 190
FEATURE                     Location/Qualifiers
misc_feature                1..190
                            note = Parabacteroides merdae 1D4
misc_difference             151..152
                            note = n is a, c, g, or t
source                      1..190
                            mol_type = other DNA
                            organism = Parabacteroides merdae
SEQUENCE: 4

```
catgatttgt agcaatacag attgatggcg accggcgcac gggtgagtaa cgcgtatgca   60
acttacctat cagaggggga tagcccggcg aaagtcggat taatacccca taaaacaggg   120
gtcccgcatg ggaatatttg ttaaagattc nncgctgata gataggcatg cgttccatta   180
ggcagttggc                                                          190
```

SEQ ID NO: 5                moltype = DNA   length = 1382
FEATURE                     Location/Qualifiers
misc_feature                1..1382
                            note = Bacteroides uniformis 3H3
misc_difference             11
                            note = n is a, c, g, or t
misc_difference             176
                            note = n is a, c, g, or t
misc_difference             249..250
                            note = n is a, c, g, or t
misc_difference             1371
                            note = n is a, c, g, or t
source                      1..1382
                            mol_type = other DNA
                            organism = Bacteroides uniformis
misc_difference             1374
                            note = n is a, c, g, or t
SEQUENCE: 5

```
tcgaggggca ncatgaactt agcttgctaa gtttgatggc gaccggcgca cgggtgagta   60
acacgtatcc aacctgccga tgactcgggg atagcctttc gaaagaaaga ttaatacccg   120
atggcatagt tcttccgcat ggtagaacta ttaaagaact tcggtcatcg atgggnatgc   180
gttccattag gttgttggcg gggtaacggc ccaccaagcc ttcgatggat aggggttctg   240
agaggaagnn cccccacatt ggaactgaga cacggtccaa actcctacgg gaggcagcag   300
tgaggaatat tggtcaatgg acgagagtct gaaccagcca agtagcgtga aggatgactg   360
ccctatgggt tgtaaacttc ttttatacgg gaataaagtg aggcacgtgt gccttttttgt   420
atgtaccgta tgaataagga tcggctaact ccgtgccagc agccgcggta atacggagga   480
tccgagcgtt atccggattt attgggttta aaggggagcgt aggcggacgc ttaagtcagt   540
tgtgaaagtt tgcggctcaa ccgtaaaatt gcagttgata ctgggtgtct tgagtacagt   600
agaggcaggc ggaattcgtg gtgtagcggt gaaatgctta gatatcacga agaactccga   660
ttgcgaaggc agcctgctgg actgtaactg acgctgatgc tcgaaagtgt gggtatcaaa   720
caggattaga taccctggta gtccacacag taaacgatga atactcgctg tttgcgatat   780
acagtaagcg gccaagcgaa agcgttaagt attccacctg gggagtacgc cggcaacggt   840
gaaactcaaa ggaattgacg ggggcccgca caagcggagg aacatgtggt ttaattcgat   900
gatacgcgag gaaccttacc cgggcttgaa ttgcaactga atgatgtgga gacatgtcag   960
ccgcaaggca gttgtgaagg tgctgcatgg ttgtcgtcag ctcgtgccgt gaggtgtcgg   1020
cttaagtgcc ataacgagcg caaccettat cgatagttac catcaggtta tgctggggac   1080
tctgtcgaga ctgccgtcgt aagatgtgag gaaggtgggg atgacgtcaa atcagcacgg   1140
cccttacgtc cggggctaca cacgtgttac aatgggggggt acagaaggca gctacacggc   1200
gacgtgatgc taatcccgaa agcctctctc agttcggatt ggagtctgca acccgactcc   1260
atgaagctgg attcgctagt aatcgcgcat cagccacggc gcggtgaata cgttcccggg   1320
ccttgtacac accgcccgtc aagccatgaa agccgggggt acctgaagtg ngtnaccgca   1380
ag                                                                  1382
```

SEQ ID NO: 6                moltype = DNA   length = 1376
FEATURE                     Location/Qualifiers
misc_difference             31
                            note = n is a, c, g, or t
misc_difference             326..327
                            note = n is a, c, g, or t
source                      1..1376
                            mol_type = other DNA
                            organism = Paraprevotella clara
misc_feature                1..1376
                            note = Paraprevotella clara 1F6
SEQUENCE: 6

```
tcgagggca gcatggactc agctttgctg ngtttgatgg cgaccggcgc acgggtgagt   60
aacgcgtatc caacctgccc tttactccgg gatagtctcc tgaaagggag tttaataccg  120
gatgtgtttg tttttccgca tgggagcgac aaataaagat taattggtaa aggatgggga  180
tgcgtcccat tagcttgttg gcggggtaac ggcccaccaa ggcgacgatg ggtaggggtt  240
ctgagaggaa ggtcccccac attggaactg agacacggtc caaactccta cgggaggcag  300
cagtgaggaa tattggtcaa tgggcnngag cctgaaccag ccaagtagcg tgaaggacga  360
cggccctacg ggttgtaaac ttcttttata agggaataaa gttcgccacg cgtggtgttt  420
tgtatgtacc ttatgaataa gcatcggcta attccgtgcc agcagccgcg gtaatacgga  480
agatgcgagc gttatccgga tttattgggt ttaaagggag cgtagcgggg cttttaagtc  540
agcggtcaaa tgccacggct caaccgtggc cagccgttga aactgtaagc cttgagtctg  600
cacagggcac atggaattcg tggtgtagcg gtgaaatgct tagatatcac gaagaactcc  660
gatcgcgaag gcattgtgcc ggggcagcac tgacgctgag gctcgaaagt gcgggtatca  720
aacaggatta gataccctgg tagtccgcac ggtaaacgat gaatgctcgc tatgggcgat  780
atattgtccg tggccaagcg aaagcgttaa gcattccacc tggggagtac gccggcaacg  840
gtgaaactca aaggaattga cggggggccc cacaagcgga ggaacatgtg gtttaattcg  900
atgatacgcg aggaacctta cccgggcttg aattgcaggt gcatgagtca gagacggctc  960
tttccttcgg gactcctgtg aaggtgctgc atggttgtcg tcagctcgtg ccgtgaggtg  1020
tcggcttaag tgccataacg agcgcaaccc ttctccccag ttgccatcgg attcgatgat  1080
gccctctggg gacactgcca tcgtaagatg cgaggaaggt ggggatgacg tcaaatcagc  1140
acggccctta cgtccggggc tacacacgtg ttacaatggg gggtacagag ggccgctgtc  1200
cggtgacggt cggccaatcc ctaaaacccc tctcagttcg gactggagtc tgcaacccga  1260
ctccacgaag ctggattcgc tagtaatcgc gcatcagcca tggcgcggtg aatacgttcc  1320
cgggccttgt acacaccgcc cgtcaagcca tgaaagccgg gggtgcctga agtccg       1376
```

```
SEQ ID NO: 7              moltype = DNA   length = 1387
FEATURE                   Location/Qualifiers
misc_feature              1..1387
                          note = Paraprevotella clara 2C7
misc_difference           8
                          note = n is a, c, g, or t
misc_difference           321..322
                          note = n is a, c, g, or t
source                    1..1387
                          mol_type = other DNA
                          organism = Paraprevotella clara
SEQUENCE: 7
gggcagcntg gactcagctt tgctgagttt gatggcgacc ggcgcacggg tgagtaacgc   60
gtatccaacc tgccctttac tccgggatag tctcctgaaa gggagtttaa taccggatgt  120
gtttttttt ccgcatggga gcgacaaata aagattaatt ggtaaaggat ggggatgcgt  180
cccattagct tgttggcggg gtaacggccc accaaggcga cgatgggtag gggttctgag  240
aggaaggtcc cccacattgg aactgagaca cggtccaaac tcctacggga ggcagcagtg  300
aggaatattg gtcaatgggc nngagcctga accagccaag tagcgtgaag gacgacggc   360
ctacgggttg taaacttctt ttataaggga ataaagtt ccacgcgtg tgttttgtat   420
gtaccttatg aataagcatc ggctaattcc gtgccagcag ccgcggtaat acggaagatg  480
cgagcgttat ccggatttat tgggtttaaa gggagcgtag cggggctttt aagtcagcgg  540
tcaaatgcca cggctcaacc gtggccagcc gttgaaactg taagccttga gtctgcacag  600
ggcacatgga attcgtggtg tagcggtgaa atgcttagat atcacgaaga actccgatcg  660
cgaaggcatt gtgccggggc agcactgacg ctgaggctcg aaagtgcggg tatcaaacag  720
gattagatac cctggtagtc cgcacggtaa acgatgaatg ctcgctatgg cgatatatt   780
gtccgtggc aagcgaaagc gttaagcatt ccacctgggg agtacgccgg caacggtgaa  840
actcaaagga attgacgggg gcccgcacaa gcggaggaac atgtggttta attcgatgat  900
acgcgaggaa ccttacccgg gcttgaattg caggtgcatg agtcagagac ggctctttcc  960
ttcgggactc ctgtgaaggt gctgcatggt tgtcgtcagc tcgtgccgtg aggtgtcggc  1020
ttaagtgcca taacgagcgc aacccttctc ccagttgcc atcgggtaat gccgggccct  1080
ctggggacac tgccatcgta agatgcgagg aaggtgggga tgacgtcaaa tcagcacgag  1140
ccttacgtcc ggggctacac acgtgttaca atgggggta cagagggccg ctgtccggtg  1200
acggtcggcc aatccctaaa acccctctca gttcggactg gagtctgcaa cccgactcca  1260
cgaagctgga ttcgctagta tcgcgcatc agccatggcg cggtgaatac gttcccgggc  1320
cttgtacaca ccgcccgtca gccatgaaa gccggggggt cctgaagtcc gtgaccgcga  1380
gggtcgg                                                           1387
```

```
SEQ ID NO: 8              moltype = DNA   length = 1377
FEATURE                   Location/Qualifiers
misc_feature              1..1377
                          note = Paraprevotella clara 2D11
misc_difference           315..316
                          note = n is a, c, g, or t
source                    1..1377
                          mol_type = other DNA
                          organism = Paraprevotella clara
SEQUENCE: 8
catggactca gctttgctga gtttgatggc gaccggcgca cgggtgagta acgcgtatcc   60
aacctgccct ttactccggg atagtctcct gaaagggagt ttaataccgg atgtgtttgt  120
ttttccgcat gggagcgaca aataaagatt aattggtaaa ggatggggat gcgtcccatt  180
agcttgttgg cggggtaacg gcccaccaag cgacgatgg gtaggggttc tgagaggaag  240
gtcccccaca ttggaactga gacacggtcc aaactcctac gggaggcagc agtgaggaat  300
attggtcaat gggcnngagc ctgaaccagc caagtagcgt gaaggacgac ggccctacgg  360
gttgtaaact tcttttataa gggaataaag ttcgccacgc gtggtgtttt gtatgtacct  420
tatgaataag catcggctaa ttccgtgcca gcagccgcg taatacgaa gatgcgagcg  480
```

-continued

```
ttatccggat ttattgggtt taaagggagc gtaggcgggc tttttaagtca gcggtcaaat   540
gccacggctc aaccgtggcc agccgttgaa actgtaagcc ttgagtctgc acagggcaca   600
tggaattcgt ggtgtagcgg tgaaatgctt agatatcacg aagaactccg atcgcgaagg   660
cattgtgccg gggcagcact gacgctgagg ctcgaaagtg cgggtatcaa acaggattag   720
ataccctggt agtccgcacg gtaaacgatg aatgctcgct atgggcgata tattgtccgt   780
ggccaagcga aagcgttaag cattccacct ggggagtacg ccggcaacgg tgaaactcaa   840
aggaattgac gggggcccgc acaagcggag gaacatgtgg tttaattcga tgatacgcga   900
ggaaccttac ccgggcttga attgcaggtg catgagtcag agacggctct ttccttcggg   960
actcctgtga aggtgctgca tggttgtcgt cagctcgtgc cgtgaggtgt cggcttaagt  1020
gccataacga gcgcaaccct tctccccagt tgccatcggg taatgccggg ccctctgggt  1080
acactgccat cgtaagatgc gaggaaggtg gggatgacgt caaatcagca cggcccttac  1140
gtccgggggct acacacgtgt tacaatgggg ggtacagagg gccgctgtcc ggtgacggtc  1200
ggccaatccc taaaacccct ctcagttcgg actggagtc gcaacccgac tccacgaagc  1260
tggattcgct agtaatcgcg catcagccat ggcgcggtga atacgttccc gggccttgta  1320
cacaccgccc gtcaagccat gaaagccggg ggtgcctgaa gtccgtgacc gcgaggg     1377
```

SEQ ID NO: 9           moltype = DNA  length = 1367
FEATURE                Location/Qualifiers
misc_feature           1..1367
                       note = Paraprevotella clara 2G11
misc_difference        7
                       note = n is a, c, g, or t
misc_difference        19
                       note = n is a, c, g, or t
misc_difference        312
                       note = n is a, c, g, or t
misc_difference        1363
                       note = n is a, c, g, or t
source                 1..1367
                       mol_type = other DNA
                       organism = Paraprevotella clara
misc_difference        1366
                       note = n is a, c, g, or t
SEQUENCE: 9

```
ggactcngct ttgctgagnt tgatggcgac cggcgcacgg gtgagtaacg cgtatccaac   60
ctgcccttta ctccgggata gtctcctgaa agggagttta ataccggatg tgtttgtttt   120
tccgcatggg agcgacaaat aaagattaat tggtaaagga tggggatgcg tcccattagc   180
ttgttggcgg ggtaacggcc caccaaggcg acgatgggta ggggttctga gaggaaggtc   240
ccccacattg gaactgagac acggtccaaa ctcctacggg aggcagcagt gaggaatatt   300
ggtcaatggg cnggagcctg aaccagccaa gtagcgtgaa ggacgacggc cctacgggtt   360
gtaaacttct tttataaggg aataaagttc gccacgcgtg gtgttttgta tgtaccttat   420
gaataagcat cggctaattc cgtgccagca gccgcggtaa tacggaagat gcgagcgtta   480
tccggattta ttgggtttaa agggagcgta ggcgggcttt taagtcagcg gtcaaatgcc   540
acggctcaac cgtggccagc cgttgaaact gtaagccttg agtctgcaca gggcacatgg   600
aattcgtggt gtagcggtga aatgcttaga tatcacgaag aactccgatc gcgaaggcat   660
tgtgccgggg cagcactgac gctgaggctc gaaagtgcgg gtatcaaaca ggattagata   720
ccctggtagt ccgcacggta aacgatgaat gctcgctatg ggcgatatat tgtccgtggc   780
caagcgaaag cgttaagcat tccacctggg gagtacgccg gcaacggtga aactcaaagg   840
aattgacggg ggcccgcaca gcggaggaa catgtggttt aattcgatga tacgcgagga   900
accttacccg ggcttgaatt gcaggtgcat gagtcagaga cggctctttc cttcgggact   960
cctgtgaagg tgctgcatgg ttgtcgtcag ctcgtgccgt gaggtgtcgg cttaagtgcc  1020
ataacgagcg caacccttct ccccagttgc catcgggtaa tgccgggccc tctgggaca  1080
ctgccatcgt aagatgcgag gaaggtgggg atgacgtcaa atcagcacgg cccttacgtc  1140
cgggggctaca cacgtgttac aatggggggt acagagggcc gctgtccggt gacggtcggc  1200
caatccctaa aacccctctc agttcggact ggagtctgca acccgactcc acgaagctgg  1260
attcgctagt aatcgcgcat cagccatggc gcggtgaata cgttcccggg ccttgtacac  1320
accgcccgtc aagccatgaa agccatgggg gcctgaagtc cgngan            1367
```

SEQ ID NO: 10          moltype = DNA  length = 29
FEATURE                Location/Qualifiers
misc_feature           1..29
                       note = 27Forward-mod-1
source                 1..29
                       mol_type = other DNA
                       organism = synthetic construct
SEQUENCE: 10

```
aatgatacgg cgaccaccga gatctacac                                     29
```

SEQ ID NO: 11          moltype = DNA  length = 53
FEATURE                Location/Qualifiers
misc_feature           1..53
                       note = 27Forward-mod-2
source                 1..53
                       mol_type = other DNA
                       organism = synthetic construct
SEQUENCE: 11

```
acactctttc cctacacgac gctcttccga tctagrgttt gatymtggct cag          53
```

SEQ ID NO: 12          moltype = DNA  length = 24

-continued

```
FEATURE              Location/Qualifiers
misc_feature         1..24
                     note = 338Reverse-1
source               1..24
                     mol_type = other DNA
                     organism = synthetic construct
SEQUENCE: 12
caagcagaag acggcatacg agat                                      24

SEQ ID NO: 13        moltype = DNA  length = 53
FEATURE              Location/Qualifiers
misc_feature         1..53
                     note = 338Reverse-2
source               1..53
                     mol_type = other DNA
                     organism = synthetic construct
SEQUENCE: 13
gtgactggag ttcagacgtg tgctcttccg atcttgctgc ctcccgtagg agt     53
```

COMPOSITION FOR INHIBITING TRYPSIN ACTIVITY CONTAINING AS ACTIVE INGREDIENT BACTERIUM BELONGING TO GENUS *PARAPREVOTELLA*

CROSS REFERENCE TO RELATED APPLICATIONS

This application is a Continuation Application of U.S. application Ser. No. 17/274,610, filed Mar. 9, 2021, which is a National Stage of International Application No. PCT/JP2019/035574 filed Sep. 10, 2019, and claims benefit from U.S. Provisional Application of 62/794,145 filed Jan. 18, 2019, and U.S. Provisional Application 62/728,908 filed Sep. 10, 2018, the contents of all of which are incorporated herein by reference in their entirety.

INCORPORATION BY REFERENCE OF SEQUENCE LISTING

The content of the electronically submitted sequence listing, file name: Q285460_Sequence_Listing_As_Filed.xml; size: 35,451 bytes; and date of creation: Marc 15, 2023, filed herewith, is incorporated herein by reference in its entirety.

TECHNICAL FIELD

The present invention relates to a composition for suppressing trypsin activity, which contains a bacterium belonging to a genus *Paraprevotella* as an active ingredient.

BACKGROUND ART

It is thought that about 100 trillion intestinal bacteria inhabit the human digestive tract. This means that far more intestinal bacteria coexist with us than about 37 trillion human somatic cells, forming an intestinal microbiota. Since the proposal of the intestinal microbiology, various studies have been conducted. In fact, recent experiments with germ-free animals have revealed that the intestinal microbiota has various effects on the maturation of the host immune system and the functions of the host. For example, intestinal bacteria contribute to the suppression of colonization and growth of pathogenic microbes by competition of the pathogenic microbes with niches. In addition, the intestinal bacteria of an obese human contain less Bacteroidetes, and germ-free mice transplanted with the feces thereof increase in body fat.

In addition, with the spread of gnotobiotic technology, detailed studies on the effects of individual bacterial species from all intestinal bacteria on the host immune system are beginning to be reported. For example, 17 bacterial strains of the Clostridia group isolated from healthy individuals induce regulatory T cells in the large intestine of a mouse and alleviate host inflammation (NPL 1). In addition, segmented filamentous bacteria (SFB) inhabiting the small intestine of a mouse adhere to the small intestinal epithelium to strongly induce Th17 cells (NPL 2). Furthermore, *Klebsiella pneumoniae* isolated from the saliva of a Crohn's disease (CD) patient ectopically colonizes the large intestine of a mouse, thereby strongly inducing Th1 cells and causing colitis (NPL 3). As above, while there are many studies on intestinal bacteria and host immune systems, there are a small number of detailed studies focusing on individual intestinal bacterial species and host-derived proteins present in feces (NPLs 4 to 7).

In addition, among host-derived proteins, trypsin is known as one of the proteolytic enzymes secreted from the pancreas. Recently, it has been suggested that residual active trypsin beyond the large intestine is involved in the onset and exacerbation of various diseases. Specifically, it has been reported that trypsin remains in the feces of patients with inflammatory bowel disease (IBD), particularly CD patients, while maintaining its activity (NPLs 8 and 9). In addition, it has been suggested that the genus *Bacteroides*, which is known as a major component of human intestinal bacteria, decreases in IBD patients (NPL 9) and that certain species of bacteria constituting the genus *Bacteroides* are involved in the inactivation of trypsin in feces (NPL 10), but there are few detailed studies.

In view of the above situation, it is expected that the isolation of bacteria capable of suppressing trypsin activity would lead to the development of bacterial therapy that suppresses trypsin activity as a new therapeutic strategy for IBD, but no such bacteria have been isolated yet.

CITATION LIST

Non Patent Literature

[NPL 1] Atarashi, K. et al. Nature 500, 232-236, doi: 10.1038/nature12331 (2013).

[NPL 2] Atarashi, K. et al. Cell 163, 367-380, doi: 10.1016/j.cell.2015.08.058 (2015).

[NPL 3] Atarashi, K. et al. Science 358, 359-365, doi: 10.1126/science.aan4526 (2017).

[NPL 4] Palm, N. W. et al. Cell 158, 1000-1010, doi: 10.1016/j.cell.2014.08.006 (2014).

[NPL 5] Kawamoto, S. et al. Immunity 41, 152-165, doi: 10.1016/j.immuni.2014.05.016 (2014).

[NPL 6] Planer, J. D. et al. Nature 534, 263-266, doi: 10.1038/nature17940 (2016).

[NPL 7] Bunker, J. J. et al. Immunity 43, 541-553, doi: 10.1016/j.immuni.2015.08.007 (2015).

[NPL 8] van de Merwe, J. P. & Mol, G. J. Digestion 24, 1-4, doi: 10.1159/000198767 (1982).

[NPL 9] Midtvedt, T. et al. PLoS One 8, e66074, doi: 10.1371/journal.pone. 0066074 (2013).

[NPL 10] Ramare, F., Hautefort, I., Verhe, F., Raibaud, P. & Iovanna,. Appl Environ Microbiol 62, 1434-1436 (1996).

SUMMARY OF INVENTION

Technical Problem

The present invention has been made in view of the above-mentioned problems of the related art, and an object thereof is to isolate a bacterium capable of suppressing trypsin activity, and to provide a composition for suppressing trypsin activity, which contains the bacterium as an active ingredient.

Solution to Problem

The present inventors have made intensive studies to achieve the above object, and as a result have identified 713 host-derived proteins by performing comprehensive protein analysis (proteome analysis) on the cecal contents of SPF mice and germ-free mice (GF mice). Compared to SPF mice, 45 proteins were significantly more abundant in the cecal contents of GF mice. Of these, attention was paid to the proteolytic enzyme trypsin (anionic trypsin-2: PRSS2), which showed a particularly significant difference in abundance.

Trypsin is a gastrointestinal enzyme secreted from the exocrine glands of the pancreas, a potent proteolytic enzyme, and has been suggested to be associated with IBD of unknown cause. With the above in mind, the expression level and secretion amount of the trypsin precursor trypsinogen in pancreatic tissues were examined, but no difference was observed between SPF mice and GF mice. On the other hand, regarding the trypsin activity in the intestinal contents, no significant difference was observed in the small intestine, but a significant decrease in activity was observed in SPF mice beyond the cecum. From the above, it was considered that the intestinal bacteria are factors that reduce the trypsin activity beyond the cecum.

Next, when fecal samples of 6 healthy volunteers were inoculated to GF mice to prepare human microbiota-colonized mice, the fecal trypsin activity was different for each sample group. Thus, the bacterial strains for reducing fecal trypsin activity were identified. The cecal contents of the human microbiota-colonized mice with the lowest trypsin activity were inoculated to other GF mice, and fecal trypsin activity was evaluated while inoculating antibiotics having various antibacterial spectra. As a result, a significant decrease in fecal trypsin activity was observed in the ampicillin-inoculated mouse group. Among them, for the mouse having the lowest trypsin activity, the bacteria contained in the cecal contents were cultured under anaerobic conditions to isolate 35 strains of the bacteria responsible for reducing trypsin activity. Furthermore, the responsible bacteria for reducing trypsin activity were narrowed down. Bacterial strains were narrowed down based on the Spearman rank correlation analysis of the relative occupancy of the intestinal bacteria and the trypsin activity value in the feces of the mouse inoculated with antibiotics having various antibacterial spectra described above. It has been clarified that the 3 bacterial strains *Paraprevotella clara* (*P. clara*), *Parabacteroides merdae* (*P. merdae*), and *Bacteroides uniformis* (*B. uniformis*) reduce trypsin activity. In addition, it has been finally found that *P. clara* monobacterium is the responsible bacterium in suppressing trypsin activity.

Furthermore, as a result of also evaluating other bacteria belonging to the genus *Paraprevotella* (*P. xylaniphila*), it has been clarified that trypsin activity can be suppressed in the same manner as in the case of *P. clara*.

The present invention has been created based on such findings, and relates to a composition for suppressing trypsin activity, which contains a bacterium belonging to a genus *Paraprevotella* as an active ingredient, and more specifically provides the following.

<1> A composition for suppressing trypsin activity, comprising: a bacterium belonging to a genus *Paraprevotella* as an active ingredient.

<2> The composition according to <1>, wherein the bacterium belonging to the genus *Paraprevotella* is at least one bacterium selected from the group consisting of *Paraprevotella clara* and *Paraprevotella xylaniphila*.

<3> The composition according to <1>, wherein the bacterium belonging to the genus *Paraprevotella* is at least one bacterium having a DNA composed of a base sequence set forth in any of SEQ ID NOs: 1 to 3 or a base sequence having at least 90% identity to the base sequence.

<4> The composition according to <1>, wherein the bacterium belonging to the genus *Paraprevotella* is at least one bacterial strain selected from the group consisting of a bacterial strain belonging to *Paraprevotella clara* specified by accession number NITE BP-02775 (*Paraprevotella clara* 1C4 strain), a *Paraprevotella clara* JCM 14859$^T$ strain, and a *Paraprevotella xylaniphila* JCM 14860$^T$ strain.

<5> The composition according to any one of <1> to <4>, further comprising: at least one bacterium selected from the group consisting of *Parabacteroides merdae* and *Bacteroides uniformis*.

<6> The composition according to <5>, wherein the *Parabacteroides merdae* is at least one bacterium having a DNA composed of a base sequence set forth in SEQ ID NO: 4 or a base sequence having at least 90% identity to the base sequence, and the *Bacteroides uniformis* is at least one bacterium having a DNA composed of a base sequence set forth in SEQ ID NO: 5 or a base sequence having at least 90% identity to the base sequence.

<7> The composition according to <5>, wherein the *Parabacteroides merdae* is a bacterial strain belonging to *Parabacteroides merdae* specified by accession number NITE BP-02776 (*Parabacteroides merdae* 1D4 strain), and the *Bacteroides uniformis* is a bacterial strain belonging to *Bacteroides uniformis* specified by accession number NITE BP-02777 (*Bacteroides uniformis* 3H3 strain).

<8> A bacterial strain belonging to *Paraprevotella clara* specified by accession number NITE BP-02775 (*Paraprevotella clara* 1C4 strain).

<9> A bacterial strain belonging to *Parabacteroides merdae* specified by accession number NITE BP-02776 (*Parabacteroides merdae* 1D4 strain).

<10> A bacterial strain belonging to *Bacteroides uniformis* specified by accession number NITE BP-02777 (*Bacteroides uniformis* 3H3 strain).

In addition, active trypsin remaining in the large intestine has long been suggested to be involved in the onset and exacerbation of symptoms of IBD known as ulcerative colitis and Crohn's disease. In light of the above, the present inventors verified the alleviation of inflammation based on the effect of suppressing the trypsin activity of the above 3 bacterial strains using a colitis model mouse. In a model in which an IL-10 gene-deficient mouse is infected with *Enterobacter aerogenes* to induce colitis, inoculation of the above 3 bacterial strains tended to suppress the onset thereof. In addition, the onset of colitis was significantly suppressed in a DSS-induced colitis model.

Therefore, based on such findings, the present invention also provides pharmaceutical compositions and methods for treating, ameliorating, or preventing the following diseases caused by trypsin activity.

<11> A pharmaceutical composition for treating, ameliorating, or preventing a disease caused by trypsin activity, comprising: at least one bacterium selected from the group consisting of a bacterium belonging to a genus *Paraprevotella, Parabacteroides merdae*, and *Bacteroides uniformis* as an active ingredient.

<12> The pharmaceutical composition according to <11>, wherein the bacterium belonging to the genus *Paraprevotella* is at least one bacterium selected from the group consisting of *Paraprevotella clara* and *Paraprevotella xylaniphila*.

<13> The pharmaceutical composition according to <11>, wherein the bacterium belonging to the genus *Paraprevotella* is at least one bacterium having a DNA composed of a base sequence set forth in any of SEQ ID NOs: 1 to 3 or a base sequence having at least 90% identity to the base sequence.

<14> The pharmaceutical composition according to <11>, wherein the bacterium belonging to the genus *Paraprevotella* is at least one bacterial strain selected from the group consisting of a bacterial strain belonging to *Paraprevotella clara* specified by accession number NITE BP-02775 (*Paraprevotella clara* 1C4 strain), a *Paraprevotella clara* JCM 14859$^T$ strain, and a *Paraprevotella xylaniphila* JCM 14860$^T$ strain.

<15> The pharmaceutical composition according to any one of <11> to <14>, wherein the *Parabacteroides merdae* is at least one bacterium having a DNA composed of a base sequence set forth in SEQ ID NO: 4 or a base sequence having at least 90% identity to the base sequence.

<16> The pharmaceutical composition according to any one of <11> to <14>, wherein the *Parabacteroides merdae* is a bacterial strain belonging to *Parabacteroides merdae* specified by accession number NITE BP-02776 (*Parabacteroides merdae* 1D4 strain).

<17> The pharmaceutical composition according to any one of <11> to <16>, wherein the *Bacteroides uniformis* is at least one bacterium having a DNA composed of a base sequence set forth in SEQ ID NO: 5 or a base sequence having at least 90% identity to the base sequence.

<18> The pharmaceutical composition according to any one of <11> to <16>, wherein the *Bacteroides uniformis* is a bacterial strain belonging to *Bacteroides uniformis* specified by accession number NITE BP-02777 (*Bacteroides uniformis* 3H3 strain).

<19> The pharmaceutical composition according to any one of <11> to <18>, wherein the disease caused by trypsin activity is inflammatory bowel disease.

<20> The pharmaceutical composition according to <19>, wherein the inflammatory bowel disease is any one of ulcerative colitis (UC) and Crohn's disease (CD).

<21> A method for treating, ameliorating, or preventing a disease caused by trypsin activity in a target by allowing the target to ingest at least one bacterium selected from the group consisting of a bacterium belonging to a genus *Paraprevotella, Parabacteroides merdae*, and *Bacteroides uniformis*.

<22> The method according to <21>, wherein the bacterium belonging to the genus *Paraprevotella* is at least one bacterium selected from the group consisting of *Paraprevotella clara* and *Paraprevotella xylaniphila*.

<23> The method according to <21>, wherein the bacterium belonging to the genus *Paraprevotella* is at least one bacterium having a DNA composed of a base sequence set forth in any of SEQ ID NOs: 1 to 3 or a base sequence having at least 90% identity to the base sequence.

<24> The method according to <21>, wherein the bacterium belonging to the genus *Paraprevotella* is at least one bacterial strain selected from the group consisting of a bacterial strain belonging to *Paraprevotella clara* specified by accession number NITE BP-02775 (*Paraprevotella clara* 1C4 strain), a *Paraprevotella clara* JCM 14859$^T$ strain, and a *Paraprevotella xylaniphila* JCM 14860$^T$ strain.

<25> The method according to any one of <21> to <24>, wherein the *Parabacteroides merdae* is at least one bacterium having a DNA composed of a base sequence set forth in SEQ ID NO: 4 or a base sequence having at least 90% identity to the base sequence.

<26> The method according to any one of <21> to <24>, wherein the *Parabacteroides merdae* is a bacterial strain belonging to *Parabacteroides merdae* specified by accession number NITE BP-02776 (*Parabacteroides merdae* 1D4 strain).

<27> The method according to any one of <21> to <26>, wherein the *Bacteroides uniformis* is at least one bacterium having a DNA composed of a base sequence set forth in SEQ ID NO: 5 or a base sequence having at least 90% identity to the base sequence.

<28> The method according to any one of <21> to <26>, wherein the *Bacteroides uniformis* is a bacterial strain belonging to *Bacteroides uniformis* specified by accession number NITE BP-02777 (*Bacteroides uniformis* 3H3 strain).

<29> The method according to any one of <21> to <28>, wherein the disease caused by trypsin activity is inflammatory bowel disease.

<30> The method according to <29>, wherein the inflammatory bowel disease is any one of ulcerative colitis and Crohn's disease.

Advantageous Effects of Invention

According to the present invention, it is possible to suppress trypsin activity. In particular, it becomes possible to suppress the intestinal trypsin activity.

BRIEF DESCRIPTION OF DRAWINGS

As shown in FIG. 13, trypsin-degrading activity was observed in all the strains. Only the above-mentioned 2 species, JCM 14859$^T$ and JCM 14860$^T$, are known as the bacteria belonging to *Paraprevotella*. From this, the trypsin-degrading activity is presumed to be an activity common to the genus *Paraprevotella*.

DESCRIPTION OF EMBODIMENTS

Figure 1:
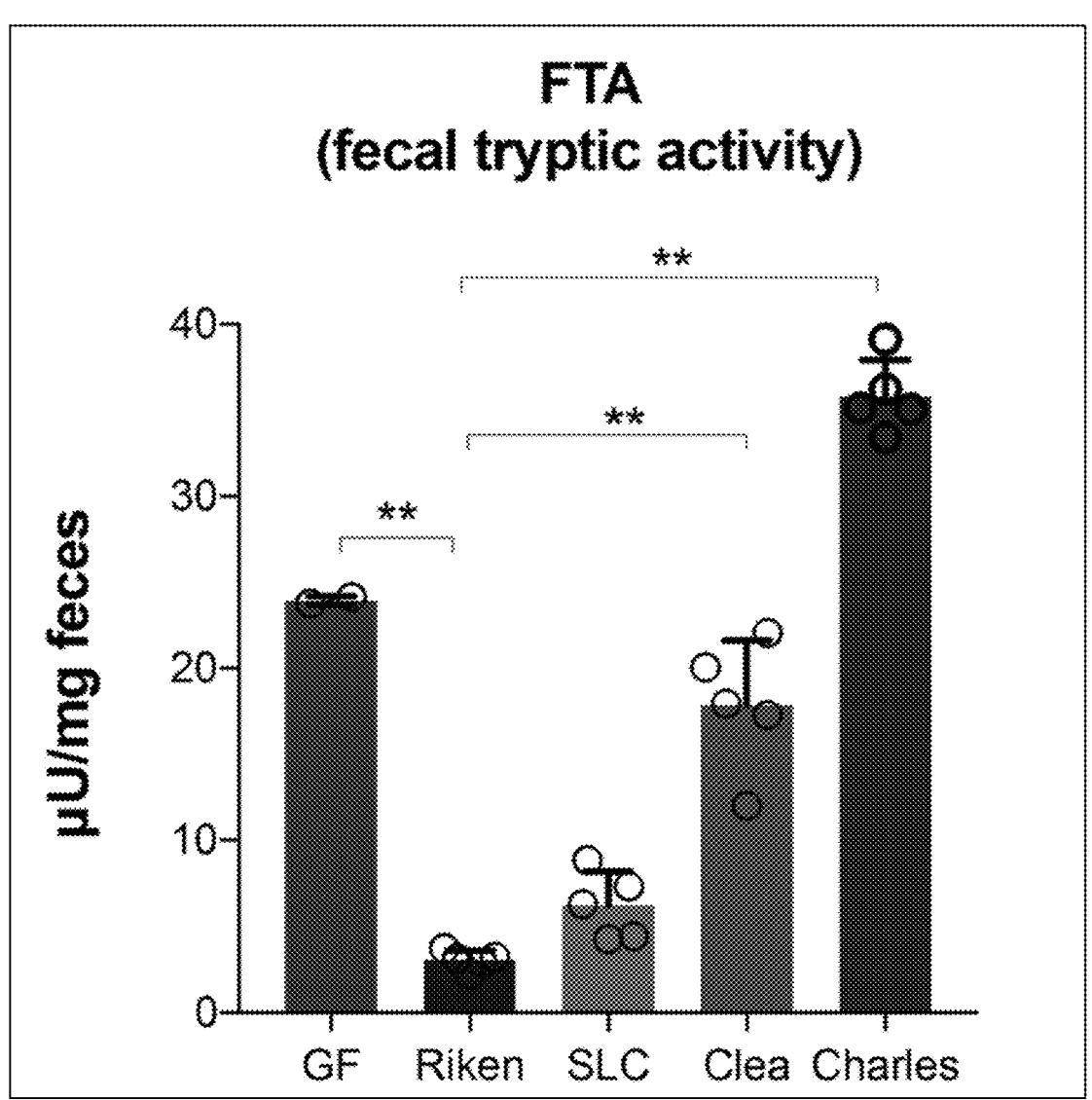
FIG. 1 is a graph showing the results of evaluating the trypsin activity in the cecal contents (feces) of SPF mice derived from different breeding facilities. In the figure, "GF," "Riken," "SLC," "Clea," and "Charles" described on the horizontal axis indicate a germ-free mouse (GF mouse), an SPF mouse maintained by RIKEN, an SPF mouse maintained by Japan SLC, Inc., an SPF mouse maintained by CLEA Japan, Inc., and an SPF mouse maintained by Charles River Laboratories Japan, Inc., and the vertical axis indicates the trypsin activity in each cecal content.
Figure 2:
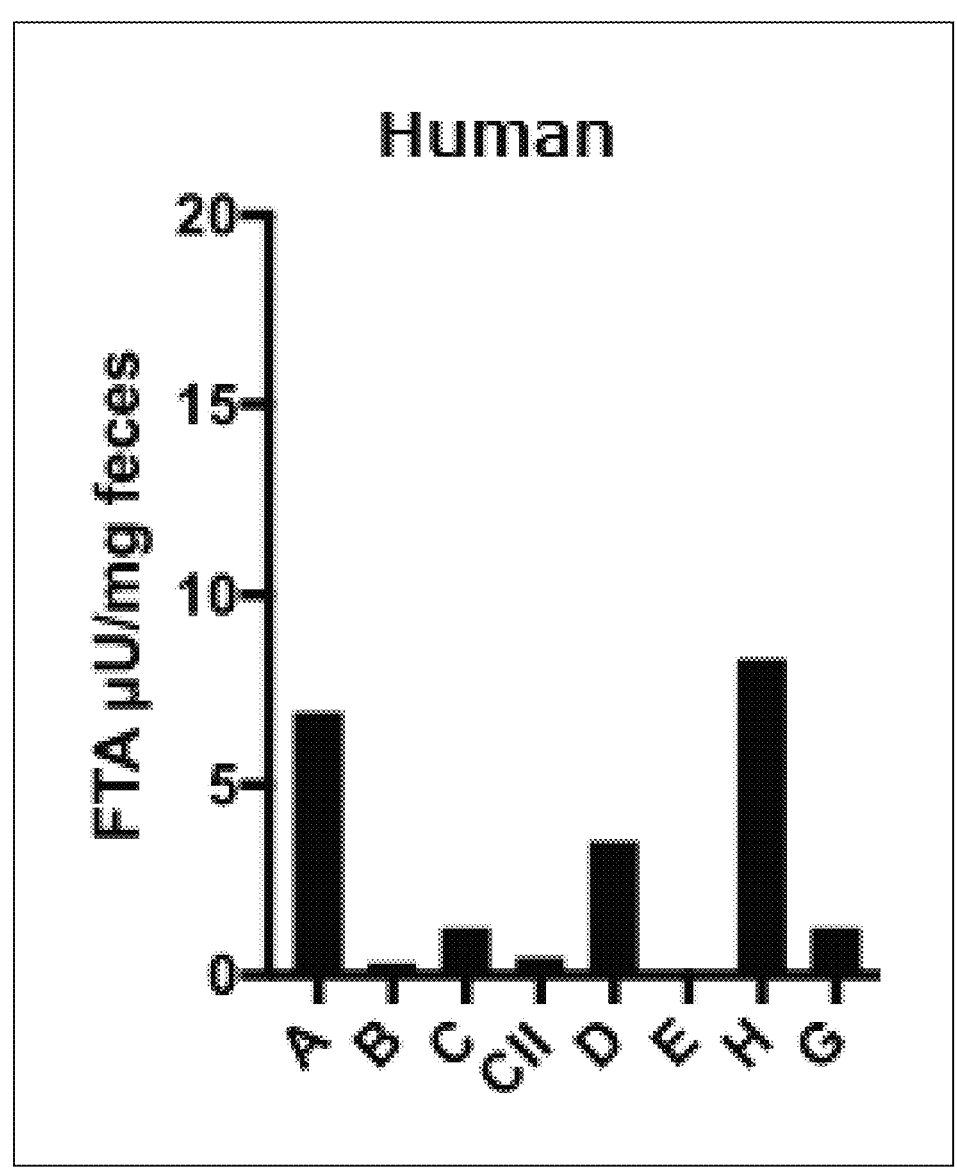
FIG. 2 is a graph showing the results of evaluating the fecal trypsin activity of healthy Japanese volunteers (A, B, C, CII, D, E, H, and G). The horizontal axis in the figure indicates each healthy volunteer, and the vertical axis indicates fecal trypsin activity. Note that the providers of the feces C and CII are the same healthy volunteer.

As shown in Examples described later, it has been revealed that a bacterium belonging to a genus *Parapre-votella* suppresses the activity of trypsin. Therefore, the present invention provides a composition for suppressing trypsin activity, which contains a bacterium belonging to a genus *Paraprevotella* as an active ingredient.

"Trypsin" is a type of endopeptidase and serine protease. In addition, it is a type of digestive enzyme contained in pancreatic juice, and has an activity of hydrolyzing the peptide bond on the carboxy group side of a basic amino acid. The trypsin whose activity is suppressed in the present invention is not particularly limited, but is preferably anionic trypsin, and more preferably anionic-trypsin-2 (PRSS2). Typically, as for PRSS2, human-derived ones include a polypeptide composed of an amino acid sequence defined by NCBI reference sequence: NP_002761 (a poly-peptide composed of an amino acid sequence encoded by a base acid sequence defined by NCBI reference sequence: NM_002770), and mouse-derived ones include a polypep-tide composed of an amino acid sequence defined by NCBI reference sequence: NP_033456 (a polypeptide composed of an amino acid sequence encoded by a base acid sequence defined by NCBI reference sequence: NM_009430). Note that the PRSS2 according to the present invention is not limited to the polypeptides specified by these typical amino acid sequences, and also includes functionally active deriva-tives thereof, functionally active fragments thereof, homo-logues thereof, variants encoded by nucleic acids that hybridize to nucleic acids encoding these polypeptides under high stringency or low stringency conditions. In addition, such derivatives, fragments, homologues, or variants include polypeptides having at least 60% (preferably 70%, more preferably 80%, further preferably 90%, more preferably 95%, and particularly preferably 99%) homology to the particular amino acid sequences.

As described above, the "trypsin activity" usually means an activity of hydrolyzing a peptide bond on the carboxy group side of a basic amino acid (lysine, arginine). However, as shown in Examples described later, in the present inven-tion, the suppression of trypsin activity is achieved by degradation of trypsin. It is also suggested in Examples described later that the degradation is induced by promoting the autolysis (autodigestion) of trypsin. Therefore, in the "trypsin activity" suppressed in the present invention, the activity of autolysis is excluded. In addition, in the present invention, the "suppression of trypsin activity" can be para-phrased as promotion of trypsin degradation or promotion of trypsin autolysis.

For example, the evaluation of the "suppression of trypsin activity" is possible by those skilled in the art by detecting the degree of degradation of a labeled substrate peptide using the label (for example, "Protease Activity Assay Kit (Abcam ab111750)" shown in Examples described later). In addition, it can also be done by assessing the degree of trypsin degradation by an immunological detection method (for example, Western blotting) that uses trypsin as the detection target, as shown in the Examples described later. Note that in the present invention, "suppression" also includes complete suppression (inhibition).

In the composition of the present invention, the "bacte-rium belonging to the genus *Paraprevotella*" contained as an active ingredient for suppressing trypsin activity includes bacteria belonging to the phylum *Bacteroides*, the class Bacteroidia, the order Bacteroidales, the family Prevotel-laceae, and the genus *Paraprevotella*, and examples thereof include *Paraprevotella clara* (*P. clara*) and *Paraprevotella xylaniphila* (*P. xylaniphila*).

Examples of *P. clara* include a bacterial strain belonging to *Paraprevotella clara* specified by accession number NITE BP-02775 (*Paraprevotella clara* 1C4 strain), and a *Paraprevotella clara* JCM 14859$^T$ strain.

Examples of *P. xylaniphila* include *Paraprevotella xylaniphila* JCM 14860$^T$ strain.

Note that the "*Paraprevotella clara* JCM 14859$^T$ strain" and the "*Paraprevotella xylaniphila* JCM 14860$^T$ strain" can be obtained from Japan Collection of Microorganisms (JCM), RIKEN BioResource Research Center (RIKEN BRC), BioResource Research Center at 3-1-1 Koyadai, Tsukuba, Ibaraki 305-0074, Japan (jcm.brc.riken.jp/en/or-dering_e).

In addition, an example of the bacterium belonging to the genus *Paraprevotella* is at least one bacterium having a DNA composed of a base sequence set forth in any of SEQ ID NOs: 1 to 3 or a base sequence having at least 90% identity to the base sequence. Note that the base sequences set forth in SEQ ID NOs: 1 to 3 indicate the 16S rRNA sequences of the *Paraprevotella clara* 1C4 strain, the *Para-prevotella clara* JCM 14859$^T$ strain, and the *Paraprevotella xylaniphila* JCM 14860$^T$ strain, respectively.

In addition to the above-mentioned bacterium belonging to the genus *Paraprevotella*, from the viewpoint of facili-tating colonization of the bacterium in the intestine, the composition for suppressing trypsin activity of the present invention may also further contain at least one bacterium selected from the group consisting of *Parabacteroides mer-dae* and *Bacteroides uniformis*

Examples of "*Parabacteroides merdae*" include a bacte-rial strain belonging to *Parabacteroides merdae* specified by accession number NITE BP-02776 (*Parabacteroides mer-dae* 1D4 strain). In addition, an example of *Parabacteroides merdae* is at least one bacterium having a DNA composed of a base sequence set forth in SEQ ID NO: 4 or a base sequence having at least 90% identity to the base sequence.

Note that the base sequence set forth in SEQ ID NO: 4 indicates the sequence of 16S rRNA of the *Parabacteroides merdae* 1D4 strain.

Examples of *Bacteroides uniformis* include a bacterial strain belonging to *Bacteroides uniformis* specified by accession number NITE BP-02777 (*Bacteroides uniformis* 3H3 strain). In addition, an example of *Bacteroides uniformis* is at least one bacterium having a DNA composed of a base sequence set forth in SEQ ID NO: 5 or a base sequence having at least 90% identity to the base sequence. The base sequence set forth in SEQ ID NO: 5 indicates the sequence of 16S rRNA of the *Bacteroides uniformis* 3H3 strain.

Note that the "at least 90% identity" in the present invention means that the identity to each base sequence is preferably 95% or more (for example, 96% or more, 97% or more, and 98% or more), and particularly preferably 99% or more.

The bacteria contained in the composition of the present invention may be live bacteria or dead bacteria. In addition, they may be substances contained in the bacteria (such as proteins, nucleic acids, lipids, sugars, and sugar chains), secretory products of the bacteria, or metabolites of the bacteria. In addition, the compositions of the present invention can be used in combination, and when ingested or absorbed in combination as a result (in the case of a combination composition), the above-mentioned bacteria can also be present separately in 2 or more compositions.

The composition for suppressing trypsin activity of the present invention can be in the form of a pharmaceutical composition (such as pharmaceuticals and quasi-drugs), food and drink (including animal feed), or a reagent used for research purposes (such as in-vitro or in-vivo experiments). In addition, since the composition of the present invention suppresses trypsin activity, it is used as a pharmaceutical composition or food and drink for treating, preventing, or ameliorating a disease caused by the activity.

The composition of the present invention can be formulated by a known pharmaceutical method. For example, capsules, tablets, pills, liquids, powders, granules, fine granules, film coating agents, pellets, troches, sublingual preparations, chews, buccal agents, pastes, syrups, suspensions, elixirs, emulsions, coatings, ointments, plasters, poultices, transdermal formulations, lotions, inhalants, aerosols, injections, suppositories, and the like can be used for inoculation by oral, parenteral (for example, intestinal, intramuscular, intravenous, intratracheal, intranasal, transdermal, intradermal, subcutaneous, intraocular, vaginal, intraperitoneal, rectal, or inhalational), or a combination of these routes.

These formulations can be appropriately combined with a pharmacologically or food and drink-acceptable carrier such as, specifically, sterilized water, physiological saline, buffer solution, medium, vegetable oil, solvent, base, emulsifier, suspension, surfactant, stabilizer, flavoring agent, air freshener, excipient, vehicle, preservative, binder, diluent, isotonic agent, soothing agent, bulking agent, disintegrant, buffer agent, coating agent, lubricant, colorant, sweetener, thickener, flavor modifier, solubilizer, or other additives.

Further, among these formulations, from the viewpoint of more efficiently suppressing trypsin activity in the intestinal tract, formulations intended for oral inoculation may be particularly combined with a composition that enables efficient delivery of the composition of the present invention into the intestinal tract. The compositions capable of such delivery into the intestinal tract are not particularly limited, and known compositions can be appropriately employed. Examples thereof include pH-sensitive compositions, compositions that suppress release to the intestinal tract (such as cellulose-based polymers, acrylic acid polymers and copolymers, and vinyl acid polymers and copolymers), bioadhesive compositions that specifically adhere to the intestinal mucosa (such as the polymer described in U.S. Pat. No. 6,368,586), compositions containing protease inhibitors, and compositions that are specifically degraded by intestinal enzymes.

In addition, when used as a pharmaceutical composition, it may further contain a known substance used for treating, preventing, or ameliorating a disease caused by trypsin activity (such as anti-inflammatory agents and immunosuppressants), or may be used in combination with such a substance.

When the composition of the present invention is used as food and drink, the food and drink may be, for example, a health food, a functional food, a food for specified health use, a food with nutritional functions, a food with functional claims, a nutritional supplement, a food for the sick, or animal feed. Specific examples of the food and drink include liquid foods such as fermented beverages, oil-containing products, soups, milk beverages, soft drinks, tea beverages, alcoholic beverages, energy drinks, and jelly-like beverages, carbohydrate-containing foods, processed livestock foods, and processed marine products; processed vegetable foods, semi-solid foods, fermented foods, confectionery, retort pouch products, and microwave oven-compatible foods. Examples also further include health foods and drinks prepared in the form of powder, granules, tablets, capsules, liquid, paste, or jelly. Note that the food and drink according to the present invention can be produced by a production technique known in the art. The food and drink may be added with ingredients (such as nutrients) effective for improving or preventing diseases caused by trypsin activity. In addition, it may be multifunctional food and drink by combining it with other ingredients or other functional foods that exhibit functions other than the improvement.

The product of the composition of the present invention (such as a pharmaceutical product, a quasi-drug, food and drink, or a reagent) or an instruction manual thereof may be labeled to be used for suppressing trypsin activity or for treating, ameliorating, or preventing diseases caused by trypsin activity. In addition, regarding the food and drink, so that the form, the target, and the like can be distinguished from those of general foods, the label of health functions as a health functional food (food for specified health use, food with nutritional functions, or food with functional claims) may be attached to the product of the composition of the present invention. Here, "product or instruction manual is labeled" means that a label is attached to the main body, container, package, or the like of the product, or that a label is attached to an instruction manual, package insert, promotional material, other printed matter, or the like that discloses product information. Further, the composition of the present invention may be in the form of a kit.

In addition, as described above, a pharmaceutical composition can be produced by a known formulation technique using the above-mentioned bacteria and the like. Therefore, the present invention also provides the use of the intestinal bacteria and the like of the present invention for producing a pharmaceutical composition for treating, ameliorating, or preventing a disease caused by trypsin activity.

<Treatment Method and the Like for Diseases Caused by Trypsin Activity>

The present invention also provides a method for suppressing trypsin activity in a target, a method for suppressing immunity in the target, or a method for treating, ameliorating, or preventing a disease caused by trypsin activity in the target, including allowing the target to ingest the above-mentioned composition or the above-mentioned bacteria serving as an active ingredient thereof (also referred to as the "pharmaceutical compositions of the present invention or active ingredients thereof").

In the present invention, the "disease caused by trypsin activity" means a disease induced by trypsin activity, and examples thereof include inflammatory bowel disease (chronic inflammatory bowel disease such as ulcerative colitis, Crohn's disease, and inflammatory bowel disease).

In the present invention, "treating, improving" includes not only complete recovery from the disease, but also alleviation of the symptoms of the disease or suppression of its progression. The "preventing" includes suppressing or delaying the onset of the disease and suppressing its recurrence.

The pharmaceutical compositions of the present invention or active ingredients thereof can be used for animals including humans as the target, but there are no particular restrictions on animals other than humans, and various domestic animals, poultry, pets, laboratory animals, and the like can be used as the target. In addition, the ingestion target of the pharmaceutical compositions of the present invention or active ingredients thereof include not only those suffering from a disease caused by trypsin activity, but also those suspected to be suffering from the disease and those in which the symptoms of the disease are alleviated or eliminated (relieved).

The method of ingesting the pharmaceutical compositions of the present invention or active ingredients thereof is not particularly limited, and may be oral inoculation or parenteral inoculation (for example, inoculation into the intestinal tract). In the case of oral inoculation, from the viewpoint of further improving the effects of the pharmaceutical compositions of the present invention or active ingredients thereof, it is preferable that the ingestion target of the pharmaceutical compositions of the present invention or active ingredients thereof reduces the production of gastric acid by ingestion of a proton-pump inhibitor (PPI) or the like.

In addition, when the pharmaceutical compositions of the present invention or active ingredients thereof are ingested, the amount ingested can be appropriately selected by those skilled in the art according to the age, weight, symptoms of the disease, health conditions, type of the composition (such as a pharmaceutical and food and drink), ingestion method, and the like.

Preferable embodiments of the composition or method for treating, ameliorating, or preventing a disease caused by trypsin activity of the present invention have been described above, but the composition or method is not limited to the above embodiments.

As shown in Examples described later, inoculation of a bacterium belonging to a genus *Paraprevotella, Parabacteroides merdae*, and *Bacteroides uniformis* tended to suppress the onset in a model in which IL-10 gene-deficient mice are infected with *Enterobacter aerogenes* to induce colitis. In addition, the onset of colitis was significantly suppressed also in the DSS-induced colitis model.

Therefore, the present invention also provides pharmaceutical compositions and methods for treating, ameliorating, or preventing the following diseases caused by trypsin activity.

A pharmaceutical composition for treating, ameliorating, or preventing a disease caused by trypsin activity, comprising: at least one bacterium selected from the group consisting of a bacterium belonging to a genus *Paraprevotella, Parabacteroides merdae*, and *Bacteroides uniformis* as an active ingredient.

A method for treating, ameliorating, or preventing a disease caused by trypsin activity in a target by allowing the target to ingest at least one bacterium selected from the group consisting of a bacterium belonging to a genus *Paraprevotella, Parabacteroides merdae*, and *Bacteroides uniformis*.

<Novel Bacteria>

As shown in Examples described later, the following 3 bacterial strains are *Staphylococcus aureus* bacterial strains isolated and cultured for the first time by the present inventors. In addition, the usefulness thereof is also as described above. Therefore, the present invention also provides the following bacterial strains.

A bacterial strain belonging to *Paraprevotella clara* specified by accession number NITE BP-02775 (*Paraprevotella clara* 1C4 strain).

A bacterial strain belonging to *Parabacteroides merdae* specified by accession number NITE BP-02776 (*Parabacteroides merdae* 1D4 strain).

A bacterial strain belonging to *Bacteroides uniformis* specified by accession number NITE BP-02777 (*Bacteroides uniformis* 3H3 strain).

Note that all of the bacterial strains were deposited at Patent Microorganisms Depositary, National Institute of Technology and Evaluation (NITE) (postal code 292-0818 2-chome-5-8 Kazusakamatari, Kisarazu, Chiba, room number 122) on Aug. 30, 2018.

EXAMPLES

Hereinafter, the present invention is described in more detail based on Examples, but the present invention is not limited to the following Examples.

In addition, the present Example was carried out using the materials and methods shown below.

(Germ-Free Mouse)

C57BL/6N Jcl gnotobiotic mice (CLEA Japan, Inc., 4 to 8 weeks of age) were bred in a breeding vinyl isolator (germ-free isolator, ICM Co., Ltd.; ICM-1B) for 1 week or more under the conditions of free water intake and feeding to acclimatize to the environment.

(SPF Mouse)

C57BL/6N SPF mice (4 to 8 weeks of age) were obtained from RIKEN BioResource Research Center, Japan SLC, Inc., CLEA Japan, Inc., or Charles River Laboratories Japan, Inc., and bred in an SPF environment under the conditions of free water intake and feeding for 1 week or more to acclimatize to the environment.

(Proteome Analysis of Cecal Contents)

The mice were sacrificed under isoflurane anesthesia, and the cecal contents were harvested and stored at −80° C. The cryopreserved sample was thawed on ice, and a 5-time weight of RIPA Lysis Buffer with protease inhibitor cocktail (Cosmo Bio; AKR-190) was added and sufficiently stirred. The mixture was centrifuged at 15,000×g for 20 minutes at 4° C. to obtain a supernatant with proteins dissolved therein.

A 30% trichloroacetic acid (TCA) solution (Nacalai Tesque, Inc.; 37211-55) in the same volume as the protein solution was mixed, which was allowed to stand at 4° C. for 30 minutes and then centrifuged at 15,000×g for 20 minutes at 4° C. to remove the supernatant, thereby obtaining a protein precipitate. The precipitate was purified by repeating redispersion and reprecipitation in acetone twice.

A 100 mM Tris-HCl pH 9.0 buffer solution (NIPPON GENE CO., LTD.; 316-90385) dissolved with final concentrations of 12 mM sodium deoxycholate (SDC, Nacalai Tesque, Inc.; 02889-72) and 12 mM sodium lauryl sulfate (SLS, Nacalai Tesque, Inc.; 31623-32) was added so that the protein concentration was 2.0 μg/μL, and sonication for 5 seconds was repeated 4 times for redissolution. TaKaRa BCA Protein Assay Kit (Takara Bio Inc.; T9300A) was used to quantify by the BCA method the concentration of protein, which was diluted to 1.0 μg/μL in the measuring cylinder.

To 20 μL of a 1.0 μg/μL protein solution, 2 μL of an aqueous solution of 100 mM dithiothreitol (Nacalai Tesque, Inc.; 14128-91) was added, and the mixture was heated at 50° C. for 30 minutes to reduce disulfide bonds. Further, 2 μL of an aqueous solution of 375 mM iodoacetamide (Nacalai Tesque, Inc.; 19302-54) was added and reacted at room temperature for 30 minutes to alkylate the thiol groups. Then, 4 μL of an aqueous solution of 400 mM cysteine (Nacalai Tesque, Inc.; 11548-52) was added and reacted for 10 minutes to quench the remaining iodoacetamide. After that, 80 μL of an aqueous solution of 50 mM ammonium hydrogen carbonate (Nacalai Tesque, Inc.; 08887-54), 2 μL of a solution of 200 ng/μL lysyl endopeptidase (Wako Pure Chemical Industries, Ltd.; 125-05061), and 2 μL of a solution of 200 ng/μL trypsin (Wako Pure Chemical Industries, Ltd.; 202-15951) were added and reacted at 37° C. overnight to form the proteins into peptide fragments.

After adding 30 μL of an aqueous solution of 5% trifluoroacetic acid (TFA, Nacalai Tesque, Inc.; 34901-21), liquid-liquid extraction was performed with 200 μL of ethyl acetate (Nacalai Tesque, Inc.; 14747-65) to remove SDC and SLS. The dissolved organic solvents were removed by centrifugal evaporator treatment. Then, 100 μL of an aqueous solution of 0.1% TFA was added, and the mixture was centrifuged at room temperature and 15,000×g for 15 minutes to remove insoluble matter. After desalting with C18 Tips (Thermo Fisher Scientific; 87782), the mixture was dissolved in an aqueous solution with final concentrations of 3% acetonitrile (Nacalai Tesque, Inc.; 00430-25) and 0.1% formic acid (Nacalai Tesque, Inc.; 08965-82). LC-MS measurement was performed using the SCIEX TripleTOF 5600 System, and proteome analysis was performed using SWATH Acquisition.

(Obtaining Mouse Feces or Human Healthy Volunteer Feces)

The feces of healthy volunteers #A to G or mouse fecal samples were diluted 5 times by weight with 20% by volume of glycerol-dissolved PBS, filtered through a 100 μm diameter filter, and stored as a stock solution at −80° C.

(Measurement of Fecal Trypsin Activity)

The frozen fecal sample were thawed at room temperature, dispersed in a 0.9% NaCl aqueous solution, and the trypsin activity of the supernatant was measured according to the protocol of Protease Activity Assay Kit (Abcam ab111750).

(Preparation of Mice Colonized with Bacteria Derived from Human Healthy Volunteer Feces)

The stock solution prepared above (Obtaining Mouse Feces or Human Healthy Volunteer Feces) was melted at room temperature and diluted with PBS to a 10-fold volume. Then, 200 μL of the diluted solution was orally inoculated into the stomach of germ-free mice. For another month, the mice were bred in a germ-free isolator under the conditions of free water intake and feeding to colonize the mice with the bacteria in the transplanted feces. In addition, the trypsin activity of these mice was also measured by the method described in the above (Measurement of Fecal Trypsin Activity).

(Preparation of Mice Colonized with Bacteria Derived from Human Healthy Volunteer Feces and Elimination of Colonized Bacteria by Antibiotic Inoculation)

In the above (Preparation of Mice Colonized with Bacteria Derived from Human Healthy Volunteer Feces), free drinking water was changed to a 200 mg/L aqueous solution of ampicillin, metronidazole, or tylosin, and the animals were bred for another month to eliminate bacteria non-resistant to each antibiotic. The fecal samples of the mice during the inoculation process were obtained by the method described above (Obtaining Mouse Feces or Human Healthy Volunteer Feces), and trypsin activity was measured by the method described above (Measurement of Fecal Trypsin Activity).

(DNA Extraction from Mouse Feces)

To 100 μl of fecal sample solution filtered with a 100 μm diameter filter, 800 μl of 10 mM Tris/10 mM EDTA buffer (pH 8.0, hereinafter referred to as TE10) dissolved with 15 mg lysozyme (Sigma-Aldrich, Lysozyme from chicken egg white; L4919) and 5 μl RNase (Thermo Fisher Scientific, PureLink RNase A (20 mg/mL); 12091-021) was added, and the mixture was shaken at 37° C. for 1 hour. Subsequently, 2,000 U of Achromopeptidase (registered trademark) (Wako; 015-09951) was added, and the mixture was shaken at 37° C. for 30 minutes for lysis.

Then, 50 μl of 20% SDS TE10 solution and 50 μl of TE10 solution dissolved with 20 mg/ml proteinase K (Roche, Proteinase K, recombinant, PCR Grade; 03115852001) were added, and the mixture was shaken at 55° C. for 60 minutes.

DNA was extracted by a liquid-liquid extraction method using Phenol/Chloroform/Isoamyl alcohol (25:24:1) (Wako; 311-90151), and bacterial genomic DNA was obtained by ethanol precipitation.

(Analysis of Microbiota in Mouse Feces)

A PCR reaction was performed on the bacterial genomic DNA using TaKaRa ExTaq (Takara Bio Inc.; RR001A) to prepare Illumina Miseq sequence amplicons for 16S rDNA. The primer sequence is as follows (Nishijima S et al DNA Res 23 125-133 2016).

```
27Forward-mod:
(5'-AATGATACGGCGACCACCGAGATCTACA

CindexACACTCTTTCCCTACACGACGCT

CTTCCGATCTAGRGTTTGATYMTGGCTCAG-3')
```

Both sequences adjacent to the index sequence are set forth in SEQ ID NOs: 10 and 11.

```
338Reverse:
(5'-CAAGCAGAAGACGGCATACGAGA

TindexGTGACTGGAGTTCAGAC

GTGTGCTCTTCCGATCTTGCTGCCTCC

CGTAGGAGT-3')
```

Both sequences adjacent to the index sequence are set forth in SEQ ID NOs: 12 and 13.

The amplicons were purified using Agencourt AMPure (registered trademark) XP (Beckman Coulter; A63882) and Min Elute PCR Purification Kit (Qiagen; 28004), and the DNA concentration of the amplicons was quantified using Quant-iT PicoGreen (registered trademark) dsDNA Assay Kit (Thermo Fisher Scientific; P7589) and KAPA library Quantification kit (Roche Diagnostics; 07960166001). The average DNA length of the mixture of amplicons was measured using the Agilent 2100 Bioanalyzer High Sensitivity DNA Kit (Agilent Technologies; 5067-4626), and the molar concentration of the amplicons was calculated. The library was denatured and a hybridization solution was prepared according to the Illumina Miseq 16S rDNA genome analysis protocol, and sequencing was performed using Miseq (Illumina; SY-410-1003) and Miseq Reagent Kit v3 (Illumina; MS-102-3003).

From the obtained sequence data, 3000 reads with high quality were randomly selected for each sample, and microbiota data was obtained by bacterial species assignment by the database assignment method for the representative sequences of operational taxonomic unit (OTU). For the database, NCBI ncbi.nlm.nih.gov/taxonomy) and RDP (rdp.cme.msu.edu/) were used, and among the top hits of GLSEARCH (nebc.nox.ac.uk/bioinformatics/docs/glsearch-.html) for each database, the most homologous results were employed for strain assignment (Nishijima S et al DNA Res 23 125-133 2016).

(Isolation of Bacteria)

The feces 12 days after inoculation of fecal samples were diluted with PBS and cultured in a 10% $CO_2$ anaerobic environment using the following media, and the colonies formed were isolated.

With EG ext. medium, mGAM medium, Schaedler medium (Wako; 517-45805), BL medium (Nissui; 5430), and CM0619 medium (Wilkins T. D. and Chalgren S. (1976) Antimicrob. Agents Chemother. 10. 926-928.) as the basal media, an agar plate of a medium supplemented with horse blood or defibrinated horse blood having a final concentration of 5% was used. In particular, as for CM0619 medium, SR0107 selective medium or SR0108 selective medium supplemented with a predetermined supplement (oxoid-.com/UK/blue/prod_detail/prod_detail.asp?pr-CM0619) was also used in the same manner.

(Creation of Phylogenetic Tree)

The package ape of the statistical analysis software R (r-project.org/) was used to create a phylogenetic tree based on the similarity of the 16S rDNA sequences of the isolated 35 bacteria based on the representative sequences of OTU used for assignment at the time of microbiota analysis.

(Suppression of Intestinal Trypsin Activity by Colonization of 35 Isolated Bacteria)

Each bacterium isolated in the above (Isolation of Bacteria) was cultured in EG ext. medium, mGAM medium, Schaedler medium, BL medium, or CM0619 medium in a 10% $CO_2$ anaerobic environment at 37° C. for 1 to 3 days. Equal volumes of the bacterial solutions that had reached the steady state were mixed, and 200 μL thereof was orally inoculated into the stomach of the germ-free mice of Example 1. The bacteria were colonized by breeding in a germ-free isolator under the conditions of free water intake and feeding. In addition, trypsin activity was measured according to the above (Measurement of Fecal Trypsin Activity).

(Spearman's Rank Correlation Analysis)

Spearman's rank correlation analysis was performed on the relative occupancy of each constituent bacterium and the fecal trypsin activity value thereof obtained from the intestinal microbiota analysis based on 16S rDNA 12 days after the fecal inoculation. The bacterial group in which the correlation coefficient ρ between the relative occupancy of the bacteria and the trypsin activity value was ρ≤−0.5 and the P-value of the uncorrelated test was P<0.05 was estimated as a candidate for trypsin activity-suppressing bacteria.

(Suppression of Intestinal Trypsin Activity by Selective Bacterial Cocktail)

In the above (Spearman's Rank Correlation Analysis), regarding the 9 bacterial strains estimated as candidates for trypsin activity-suppressing bacteria, bacterium-colonized mice were prepared and their intestinal trypsin activity was measured according to the method described above (Suppression of Intestinal Trypsin Activity by Colonization of 35 Isolated Bacteria). In addition, the 9 bacterial strains were divided into 3 *Bacteroides* bacterial strains and 6 non-*Bacteroides* bacterial strains, and bacterium-colonized mice were prepared and their intestinal trypsin activity was measured.

(Suppression of Ulcerative Colitis (UC)-Like Inflammation by Colonization 6 of Trypsin Activity-Suppressing Bacterial Cocktail)

IL10−/− mice (4 to 8 weeks of age, The Jackson Laboratory) were aseptically bred according to the method described above (germ-free mice). In addition, 3 isolated *Bacteroides* bacterial strains or 6 non-*Bacteroides* bacterial strains were orally inoculated and colonized according to the method described above (Suppression of Intestinal Trypsin Activity by Selective Bacterial Cocktail). One week after the oral inoculation, UC-like inflammation-inducing treatment was performed according to the following procedure. The *K. aeromobilis* 11E12 strains (Atarashi K. et al Science 358, 359 2017) isolated from UC patients were cultured in Schaedler medium at 37° C. in a 10% $CO_2$ anaerobic environment for 1 to 3 days, and 1 to 2×10⁸ CFU/200 μl of the bacterial solution that had reached the steady state was orally inoculated into the stomach of the mice. Subsequently, they were bred in a germ-free isolator under the conditions of free water intake and feeding for another 3 weeks to colonize the bacteria. The intestinal trypsin activity was measured 3 weeks after the inoculation of the 11E12 strains according to the method described above (Measurement of Fecal Trypsin Activity). In addition, as an index of inflammation, the fecal level of Lipocalin-2 was measured by the ELISA method (abcam; Mouse Lipocalin-2 ELISA Kit; ab199083).

(Suppression of Trypsin Activity by Cultured Bacteria)

To the culture solution of each of the 9 bacteria selected in the above (Spearman's Rank Correlation Analysis) that had reached the steady state after culturing in a 10% $CO_2$ anaerobic environment at 37° C. for 1 to 3 days, a trypsin-containing solution obtained by diluting the cecal contents of germ-free mice 50-fold with germ-free water was mixed in the same volume, which was further cultured under the same conditions for 12 hours.

Centrifugation was carried out at 10,000×g for 15 minutes to obtain a supernatant free of bacterial cells. They were mixed with a loading buffer (BioRad; 1610739), and after mercaptoethanol reduction and heat denaturation treatment, SDS-tricine PAGE was performed. Subsequently, a voltage was applied in Tris-glycine buffer and transferred to Immobilon-P Transfer Membrane (Merck; ISEQ07850). The anti-anionic trypsin-2 rabbit antibody was used as the primary antibody, and Anti-IgG (H+L chain) (Rabbit) pAb-HRP (MBL; Code No. 458) was used as the secondary antibody, and the presence or absence of the anionic trypsin-2 protein was confirmed using chemiluminescence by Chemi-Lumi One Super (Nacalai Tesque, Inc.; 02230-14).

(Suppression of Trypsin Activity by *Paraprevotella* Bacteria)

JCM 14859$^T$ (*P. clara* strain) and JCM 14860$^T$ (*P. xylaniphila* strain) were obtained from Japan Collection of Microorganisms (JCM), RIKEN BioResource Research Center (RIKEN BRC), and were each cultured in EG ext. medium under 37° C. and 10% $CO_2$ anaerobic environment for 1 to 3 days. The bacterial solution that had reached the steady state was treated according to the method described above (Suppression of Trypsin Activity by Cultured Bacteria), and the degrading activity of trypsin was evaluated from the results of Western blotting.

(Crosslink Test Between *P. Clara*-Derived Protein and Trypsin)

First, 25 µl of 150 µg/ml mPRSS2/PBS solution, 150 µl of *P. clara* 1C4 strain (OD600>1.0) that had been cultivated in EGEF medium under anaerobic conditions and had reached the steady phase, and 75 µl of fresh EGEF medium were mixed and incubated at 37° C. for 35 minutes. Centrifugation was carried out at room temperature at 4,000×g for 5 minutes, and the supernatant was collected (corresponding to the "supernatant" sample in FIG. 14). After redispersing the bacteria in 800 µl of PBS, they were centrifuged at 4,000×g at room temperature to remove the supernatant, thereby removing the unadsorbed mPRSS2 protein. The bacteria were redispersed in 250 µl of an aqueous solution of 10 mM DSSO/PBS and allowed to stand at room temperature for 15 minutes to form random covalent crosslinks in the bacterial constituents and adsorbents. Further, 30 µl of an aqueous solution of 200 mM Tris-HCl (pH 8.0) was added, and the mixture was allowed to stand at room temperature for 5 minutes to quench the unreacted DSSO. Centrifugation was carried out at under the conditions of 4,000×g and room temperature for 5 minutes, and the supernatant was removed. After redispersing the bacteria in 800 ul of PBS, they were centrifuged under the same conditions, and the supernatant was removed and washed. The bacteria were disrupted by adding a cell lysate having a 1% SDS/10 mM Tris-HCl (pH 8.0)/5 mM EDTA composition, and then were centrifuged under the conditions of 20,000×g at 4° C. for 5 minutes to obtain a cell disruption solution as a supernatant (corresponding to the "Pellet" sample in FIG. 14). The supernatant sample and the Pellet sample were subjected to Western blotting, and the mPRSS2-specific antibody was detected by chemiluminescence to detect the protein bound to mPRSS2. Note that the reagents and the like used in the present method are as follows.

mPRSS2: mouse recombinant PRSS2 protein (His Tag) (Sino biological 50383-M08H)

DSSO: disuccinimidyl sulfoxide (Thermo Fisher Scientific A33545)

SDS: prepared from 10%-SDS solution (Nacalai Tesque, Inc. 30562-04)

Tris-HCl: prepared from 1 mol/l-Tris-hydrochloric acid buffer solution (pH 8.0) (Nacalai Tesque, Inc. 06938-44)

EDTA: prepared from 0.5 mol/l-EDTA solution (ph8.0) (Nacalai Tesque, Inc. 06894-14)

PBS: Dulbecco phosphate-buffered saline (free of Ca and Mg) (Nacalai Tesque, Inc. 14249-95)

Primary antibody for WB detection: Anti-6-His, Rabbit-Poly (Funakoshi Co., Ltd. A190-114A, used after diluting 400 times)

Secondary antibody for WB detection: Anti-IgG (Rabbit) pAb-HRP (MBL Code No. 458, used after diluting 400 times)

WB detection reagent: Chemi-Lumi One L (Nacalai Tesque, Inc. 07880-54).

(Trypsin Activity Inhibition Test)

A 5-fold mol amount of TLCK DMSO solution was added to an aqueous solution of 1 mg/ml hPRSS2/PBS and allowed to stand at room temperature for 3 hours to obtain TLCK-modified TLCK-hPRSS2 having no trypsin activity. Unreacted TLCK was removed by Sephadex-G25 column chromatography, and TCLK-hPRSS2 was purified by concentration with an ultrafiltration membrane. The bacteria *P. clara* that had reached the steady state after culturing in EGEF medium under anaerobic conditions were centrifuged at room temperature at 4,000×g for 5 minutes to redisperse the bacteria in PBS, and then, centrifugation and supernatant removal under the same conditions were performed once more to obtain bacteria from which the EGEF medium component had been removed. The bacteria dispersed in PBS and the TCLK-hPRSS2/PBS solution were mixed and allowed to stand for 3 hours in an anaerobic 37° C. environment under the conditions of 20 ng/µl TLCK-hPRSS2 and the bacterial concentration OD=0.9. The bacterial solution was centrifuged at room temperature at 4,000×g for 5 minutes, and hPRSS2 in the supernatant was detected by Western blotting. The reagents and the like used in the present method are as follows.

hPRSS2: human PRSS2/trypsin 2 protein (recombinant) (LSBio LS-G20167-5)

TLCK: trypsin inhibitor tosyl-L-lysyl-chloromethane hydrochloride (ABCAM ab144542)

Sephadex-G25: Prepack Disposable PD-10 Column (GE Healthcare 17085101)

Primary antibody for WB detection: Anti-PRSS2/Trypsin 2 antibody IHC-plus (LSBio LS-B15185-50, used after diluting 400 times)

Secondary antibody for WB detection: Anti-IgG (Rabbit) pAb-HRP (MBL Code No. 458, used after diluting 400 times)

WB detection reagent: Chemi-Lumi One L (Nacalai Tesque, Inc. 07880-54).

Example 1

[Abundant Active Trypsin in Feces of Germ-Free Mice]

Comprehensive protein analysis (shotgun proteomics, proteome analysis) of the cecal contents of SPF mice (RIKEN SPF mice) and GF mice maintained at RIKEN was performed.

As a result, although not shown in the figure, 713 host-derived proteins were detected, and among them, 45 proteins were significantly abundant in the cecal contents of the GF mice. Among these, attention was paid to the proteolytic enzyme trypsin (anionic trypsin-2: PRSS2), which is particularly abundant and has been reported to be associated with IBD.

Next, the activity of trypsin in the feces of RIKEN SPF mice and GF mice was measured, and the amount of protein was evaluated based on Western blotting (WB).

As a result, although not shown in the figure, the trypsin activity was significantly higher in the GF mice than in the RIKEN SPF mice. In addition, the amount of trypsin protein was higher in the GF mice. Furthermore, when the cross section of the intestinal tract of the distal large intestine of the RIKEN/SPF mice and GF mice was observed by immunohistochemical staining, a large amount of trypsin was present in the GF mice.

From the above, it has been found that more active trypsin is present in the large intestine beyond the cecum of the GF mice as compared with the RIKEN SPF mice.

[Abundant Active Trypsin in Feces of Inflammatory Bowel Disease and Inflammation Model Mice]

The activity of trypsin was measured and the amount of its protein was evaluated on the fecal samples of Japanese IBD patients suffering from ulcerative colitis (UC) and Crohn's disease (CD). As comparison targets, fecal samples of healthy Japanese volunteers were evaluated. As a result, although not shown in the figure, significantly more active trypsin was observed in the feces of UC and CD patients as compared with the feces of healthy individuals.

In addition, when the fecal trypsin activity during inflammation of IL-10 gene-deficient mice (IL10−/− mice) known as colitis model mice was evaluated, the trypsin activity was significantly higher than the fecal trypsin activity of WT mice. It has been reported that active trypsin remaining in the large intestine may be involved in the onset of IBD and the exacerbation of its pathological condition. The above series of results supports the existing reports.

[Active Trypsin Activity Remains Beyond Cecum in GF Mice]

The trypsin activity of each site in the digestive tract was compared between RIKEN SPF mice and GF mice. As a result, although not shown in the figure, no significant difference was observed between the two in the small intestine, but it was significantly higher in the GF mouse beyond the cecum. In addition, when the expression level and secretion amount of the trypsin precursor trypsinogen (PRSS2) in the pancreatic tissues mainly responsible for the secretion of trypsin were confirmed by RT-qPCR and WB, no significant difference was observed between the two.

From the series of results, it is considered that the increase in trypsin activity in GF mice beyond the cecum is due to the abnormal residual of trypsin normally secreted from pancreatic tissues. One of the factors is considered to be the involvement of intestinal bacteria that colonize beyond the cecum. That is, it was assumed that in SPF mice, intestinal bacteria colonized beyond the cecum controlled the function of reducing active trypsin, and in GF mice, active trypsin remained due to the absence of intestinal bacteria.

[Intestinal Microbiota Beyond Cecum of Mice Affects its Trypsin Activity]

It is known that the intestinal microbiota of SPF mice is uniquely maintained in each breeding facility. Therefore, in order to evaluate the relationship between the colonized intestinal bacteria beyond the cecum and its trypsin activity, the trypsin activity in the cecal contents and its microbiota were evaluated for SPF mice derived from different breeding facilities. RIKEN·SPF mice and SPF mice maintained by Japan SLC, Inc., Charles River Laboratories Japan, Inc., and CLEA Japan, Inc. (hereinafter, SLC·SPF mice, Charles·SPF mice, and Clea SPF mice) were compared.

As a result, as shown in FIG. 1, regarding the trypsin activity in the cecal contents, RIKEN·SPF mice and SLC·SPF mice were similarly at a low level, and Charles·SPF and Clea·SPF mice were significantly higher than the mice at the former 2 institutions. In addition, although not shown in the figure, regarding the intestinal microbiota, a significant difference was observed on Uni-Frac-PCoA between the 2 groups of RIKEN·SPF mice and SLC·SPF mice and the 2 groups of Charles·SPF mice and Clea·SPF mice. From the above, it has been found that the difference in the intestinal microbiota due to the difference in the breeding environment affects the trypsin activity beyond the cecum. In addition, it has been suggested that specific intestinal bacterial species may reduce trypsin activity.

[Intestinal Bacteria of Healthy Individuals Reduce Trypsin Activity in Mice]

The above studies suggest that specific intestinal bacterial species may reduce trypsin activity beyond the cecum, which is suspected to be involved in colon inflammation, in mice. Based on this hypothesis, by colonizing a specific intestinal bacterial species beyond the cecum, trypsin activity can be suppressed, which in turn can be expected to alleviate inflammation of the large intestine. Therefore, assuming future clinical applications, investigation was made on the control of trypsin activity using human-derived intestinal bacteria.

First, the feces of healthy Japanese volunteers (donors A to F) were orally inoculated into the stomach of GF mice to prepare human microbiota-transplanted mice (A to F), and the fecal trypsin activity was evaluated.

Figure 3:
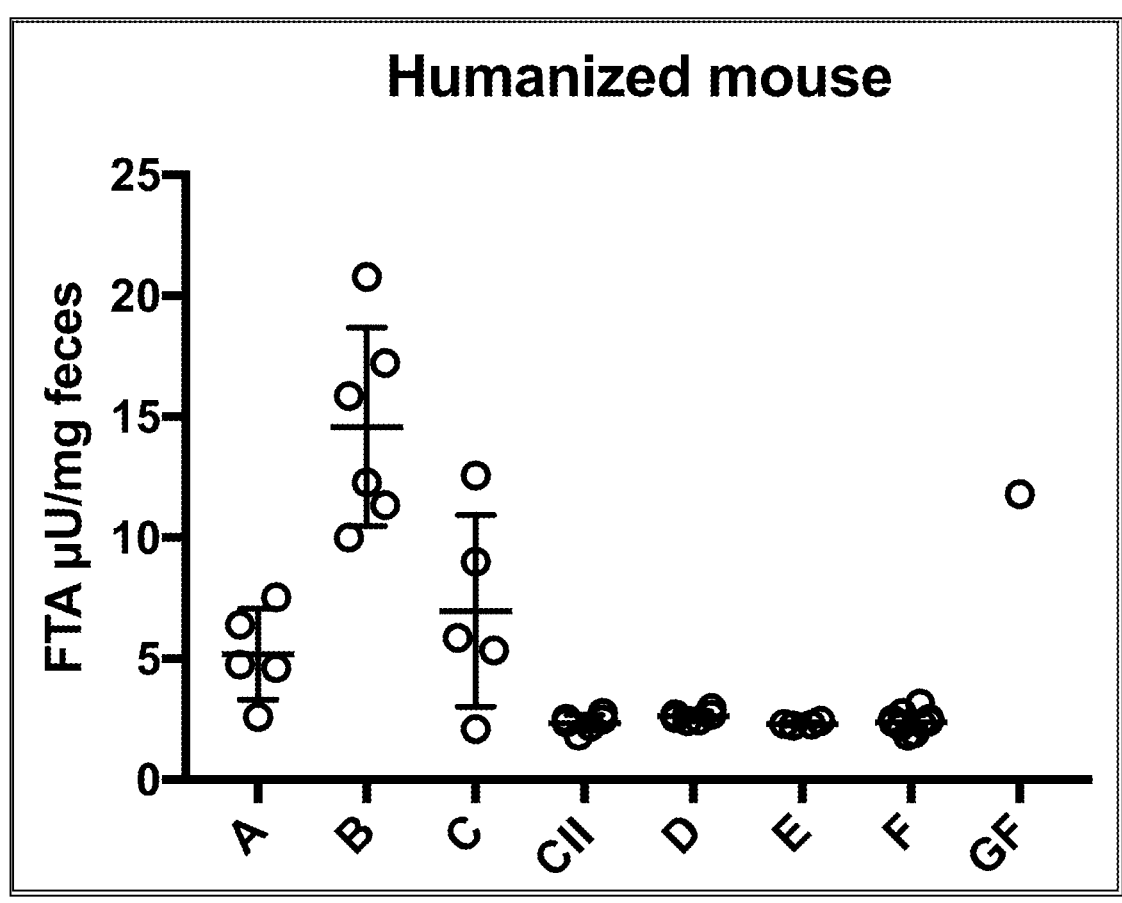
FIG. 3 is a graph showing the results of evaluating fecal trypsin activity by orally inoculating the feces of the healthy Japanese volunteers (A to F) into the stomach of GF mice to prepare human microbiota-transplanted mice (A to F). The horizontal axis in the figure indicates human microbiota-transplanted mice and GF mice, and the vertical axis indicates fecal trypsin activity.

As a result, as shown in FIG. 3, the mouse fecal trypsin activity was as low as that in the case of RIKEN SPF mice, except for B. From this, it has been found that there are human-derived intestinal bacterial species that reduce the activity of mouse trypsin.

Example 2

[35 Bacterial Strains Derived from Feces of Healthy Individuals Reduce Trypsin Activity in Mouse Feces]

For the feces of healthy volunteer C which had showed particularly low trypsin activity in the above investigation, search was made for bacterial species that reduce trypsin activity beyond the cecum. The feces of healthy volunteer C was orally inoculated into the stomach of GF mice, and 24 hours later, the antibiotics ampicillin (Amp), tylosin, or metronidazole (MNZ) were inoculated by free drinking water.

Figure 4:
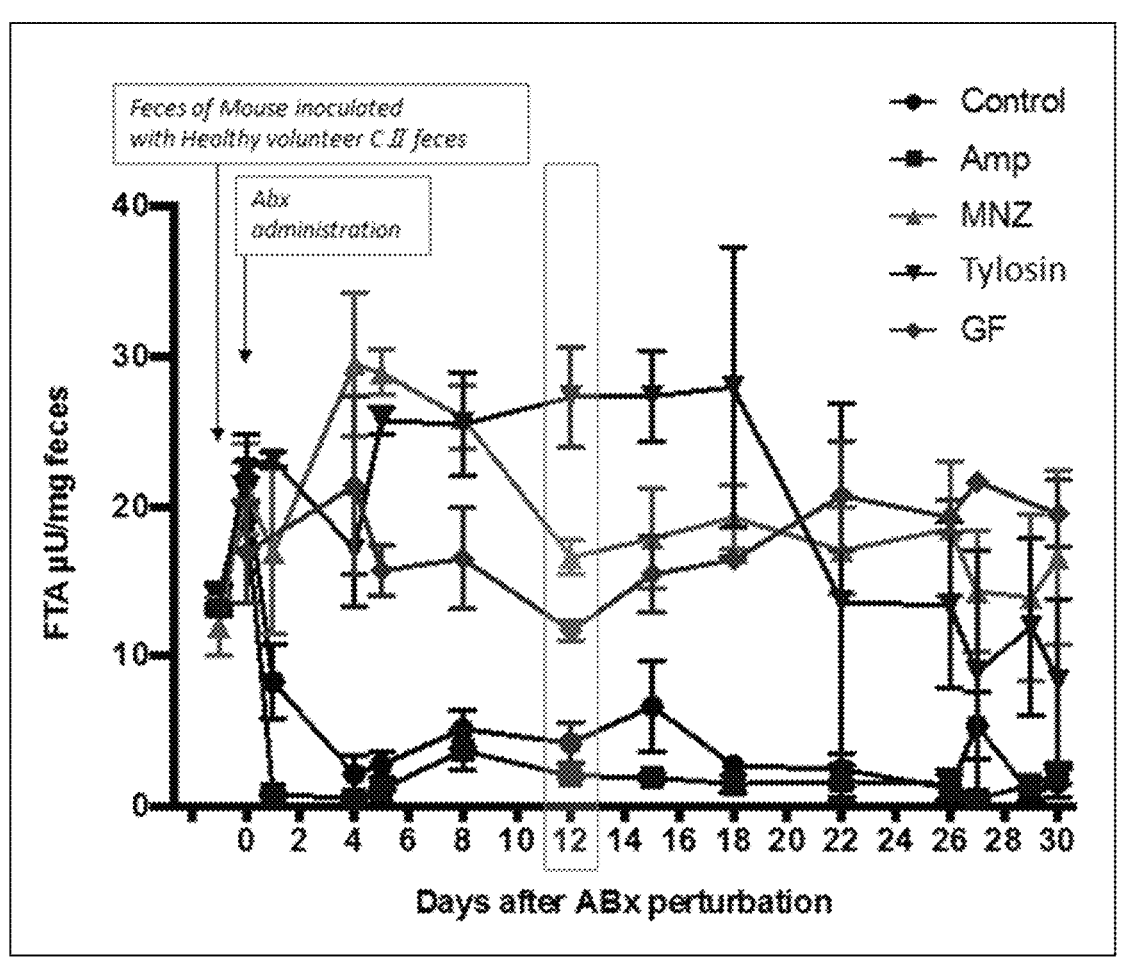
FIG. 4 is a graph showing the results of evaluating the fecal trypsin activity over time on the GF mice that were orally inoculated with the feces CII of the healthy volunteer into the stomach, and 24 hours later were inoculated by free water intake with the antibiotics (Abx) ampicillin (Amp), tylosin, or metronidazole (MNZ). The horizontal axis in the figure indicates the number of days after inoculation of the antibiotics, and the vertical axis indicates fecal trypsin activity. Note that the figure also shows the results of evaluating the GF mice (control) inoculated with only the feces CII of the healthy volunteer (no antibiotics inoculated) and the GF mice (GF) inoculated with neither feces nor antibiotics. The number of individuals evaluated is as follows. Control:Amp:MNZ:Tylosin:GF=4:5:5:4:2. Since the tendency of the activity transition at the time of Amp inoculation was the same as that of the antibiotic non-inoculated group (control), the bacterial group contributing to the decrease in activity was presumed to be Amp-resistant bacteria. Based on the above, the bacteria were isolated and cultured from the fecal samples of the Amp-inoculated group to obtain a total of 35 bacterial strains shown in FIG. 5 below. Subsequently, the microbiota of each individual on the 12th day from the start of antibiotic inoculation was derived by meta-16S rDNA analysis. Furthermore, a correlation analysis was performed on the relative occupancy of each of the bacterial species constituting the microbiota and the trypsin activity value of that individual, to thereby estimate the bacterial species contributing to the decrease in trypsin activity.

As a result, as shown in FIG. 4, the fecal trypsin activity was significantly reduced in the antibiotic non-inoculated group and the ampicillin-inoculated group as compared with those before the bacterial inoculation. On the other hand, in the tylosin-inoculated group and the metronidazole-inoculated group, the fecal trypsin activity was maintained high. From the above results, it has been found that the intestinal bacterial species that reduce trypsin activity are resistant to ampicillin and sensitive to tylosin and metronidazole.

Figure 5:
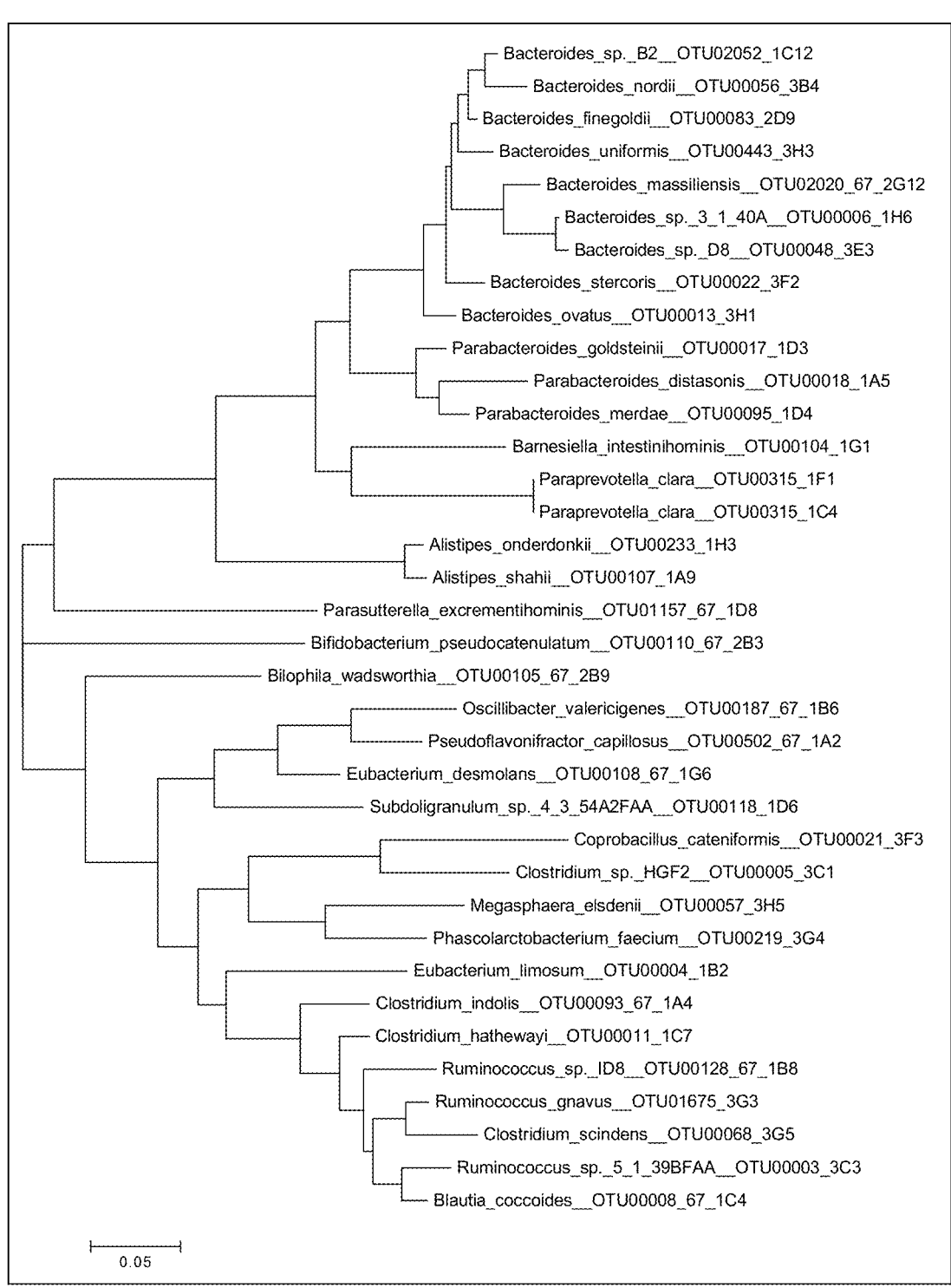
FIG. 5 shows a phylogenetic tree based on the homology of 16S rDNA sequences of a total of 35 bacterial strains isolated from the fecal samples of the Amp-inoculated group shown in FIG. 4. The notation in the figure shows, in order from the left, the name of bacterial species assigned, the representative OTU No. of 16S rDNA analysis, and the named isolated bacterial strain.

Subsequently, the cecal contents of the individual with the lowest trypsin activity value in the ampicillin-inoculated group were cultured in a medium having a different composition in an anaerobic chamber to obtain a total of 432 colonies. As a result of bacterial strain collation based on 16S rRNA analysis, it was revealed that 35 bacterial strains of human intestinal bacteria derived from the feces of donor C had been isolated as shown in FIG. 5.

Since the 35 isolated bacterial strains account for about 80% of the bacterial species constituting the intestinal microbiota of the feces of donor C, it can be expected that a similar microbiota and environment will be formed in the intestine of donor C by inoculation to GF mice. Therefore, a bacterial solution obtained by individually culturing and mixing these 35 bacterial strains (hereinafter, 35-mix) was orally inoculated into the stomach of GF mice, and the trypsin activity beyond the cecum was evaluated over time.

Figure 6:
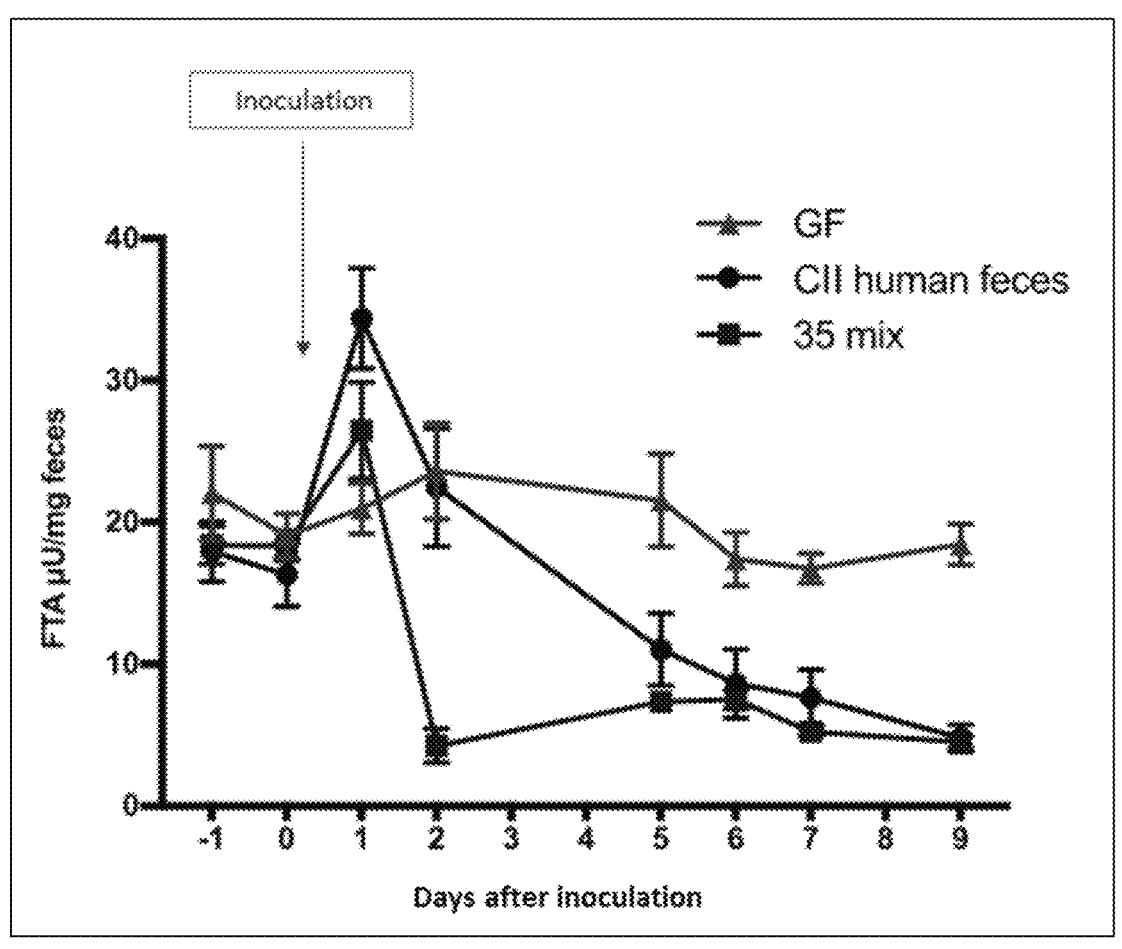
FIG. 6 is a graph showing the results of evaluating over time the fecal trypsin activity of mice colonized with the isolated 35 bacteria. The horizontal axis in the figure indicates the number of days after inoculation of the bacteria or feces, and the vertical axis indicates fecal trypsin activity. The isolated 35 bacteria were inoculated to GF mice ("35 mix" in the figure) to evaluate the intestinal trypsin activity, and the same or better effects were observed as compared with the transplantation of bacteria-derived feces ("CII human faces" in the figure).

As a result, as shown in FIG. 6, the fecal trypsin activity was significantly decreased 2 days after the inoculation of 35-mix. Even on the 9th day of inoculation, the amount of active trypsin in the feces was maintained at a low level.

From the above results, it has been found that inoculation of 35-mix reduces the activity of trypsin beyond the cecum in mice.

[9 Bacterial Strains Isolated from Feces of Healthy Individuals Reduce Trypsin Activity in Mouse Feces]

Among the above-mentioned 35 bacterial strains having the function of reducing trypsin activity, the responsible bacteria controlling the function were identified. Specifically, in an investigation to colonize GF mice with bacteria derived from the feces of healthy volunteer donor C while inoculating various antibiotics, 12 days after antibiotic inoculation, Spearman's rank correlation analysis of the relative occupancy of intestinal bacteria and the fecal trypsin activity value based on 16S rRNA analysis was performed.

Figure 7:
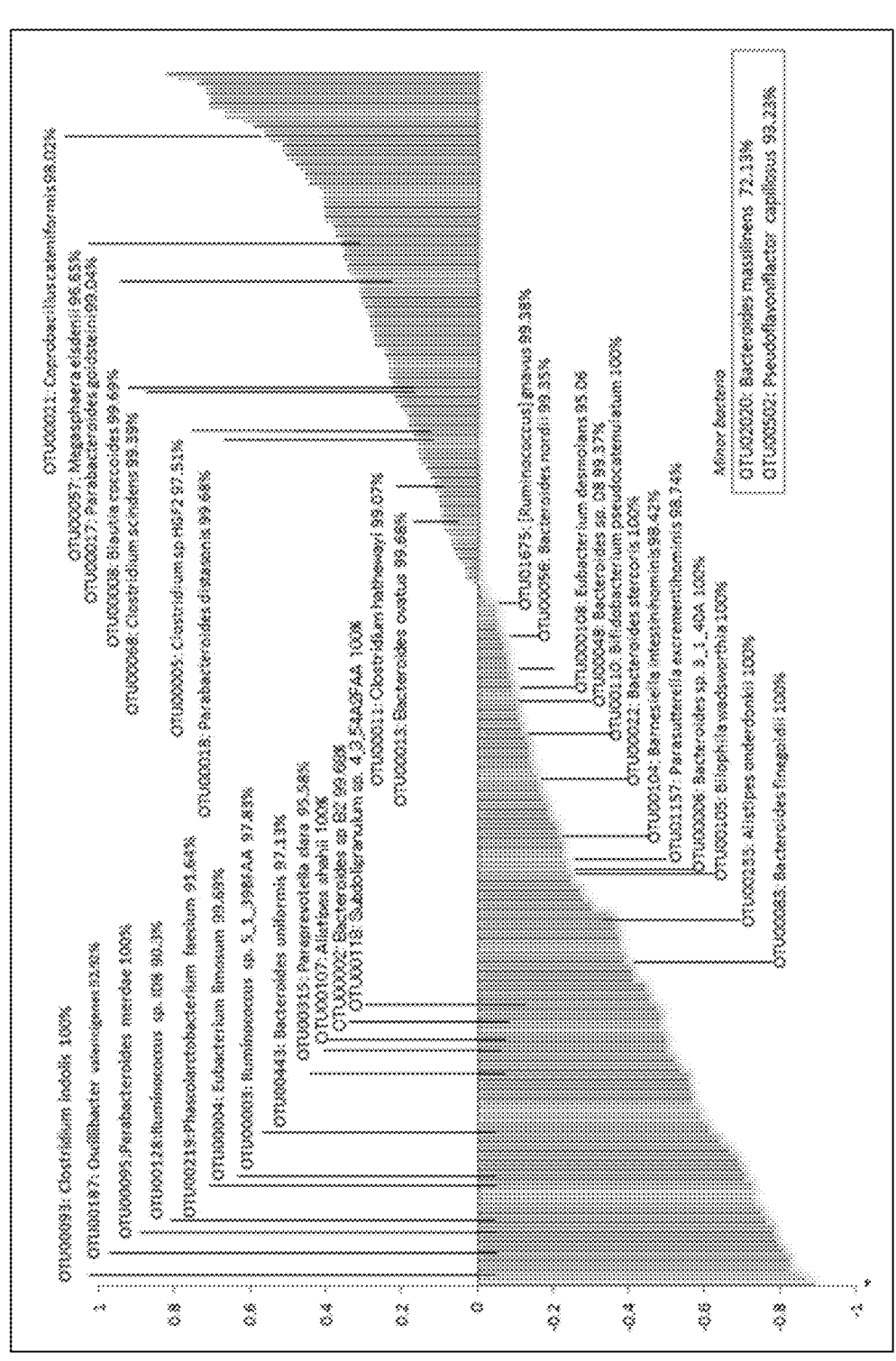
FIG. 7 is a diagram showing Spearman's correlation of microbiota and trypsin activity. More specifically, it is a diagram showing the results of expressing the bacterial species whose uncorrelated test P-value satisfies P<0.05 in the ascending order of the correlation coefficient ρ. Spearman's correlation was used to estimate the bacterial strains whose abundance was correlated with the fecal trypsin activity value of each individual. Of these, attention was paid to 9 bacterial strains with a strong negative correlation (9 bacteria from the left).
Figure 8:
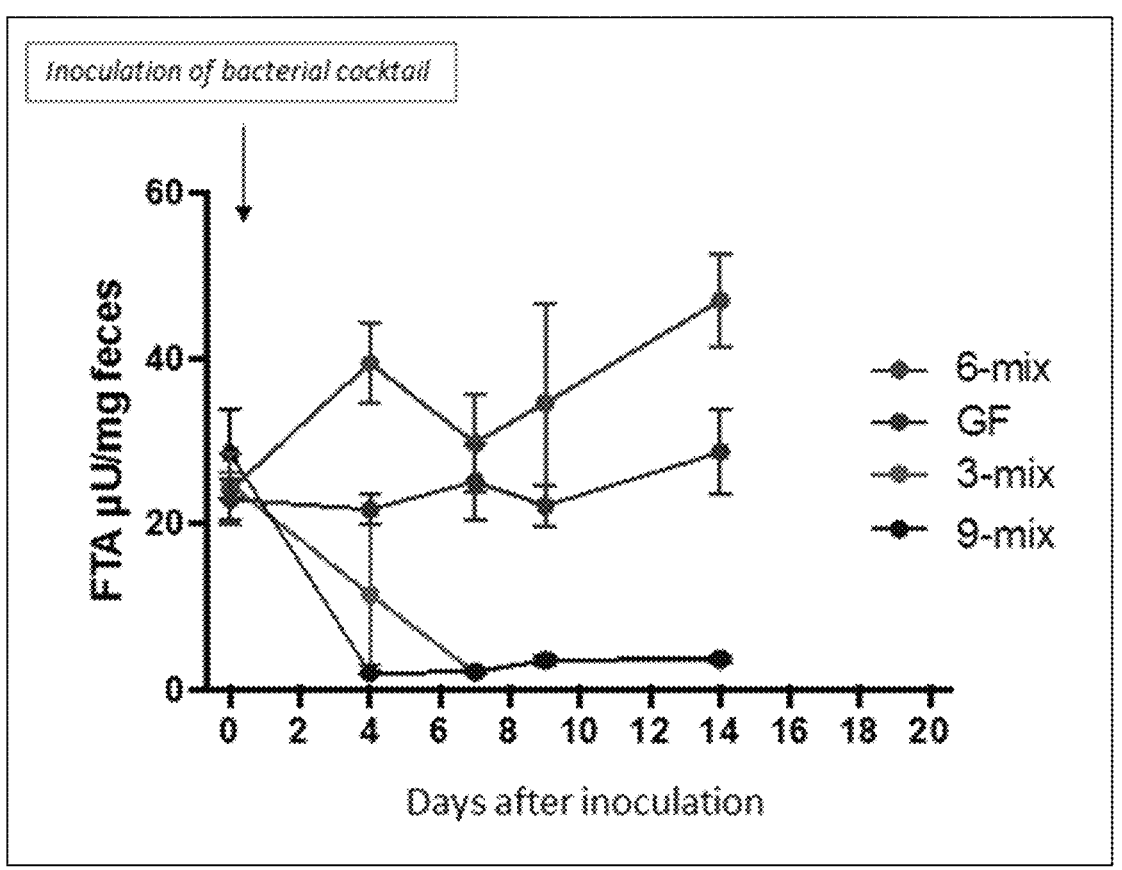
FIG. 8 is a graph showing the results of evaluating over time the fecal trypsin activity of mice colonized with the 9 bacterial strains (9-mix) observed to have a strong negative correlation in Spearman's correlation shown in FIG. 7. Further, the mice colonized with the 6 bacterial strains (6-mix) or 3 bacterial strains (3-mix) shown in FIG. 9 below were also evaluated in the same manner. The horizontal axis in the figure shows the number of days since each bacterial cocktail was inoculated, and the vertical axis shows the fecal trypsin activity.

As a result, in the Spearman rank correlation analysis shown in FIG. 7, among the bacterial strains showing a negative correlation with fecal trypsin activity, attention was particularly paid to 9 bacterial strains having a significant probability of correlation coefficient of p<0.05. Next, a bacterial solution obtained by individually culturing and mixing the 9 bacterial strains (hereinafter, 9-mix) was orally inoculated into the stomach of GF mice, and the activity of trypsin in the feces and the amount of its protein were evaluated. As a result, as shown in FIG. 8, the fecal trypsin activity was significantly reduced in the 9-mix inoculation group. In addition, although not shown in the figure, the amount of active trypsin protein was reduced below the detection limit of WB. From the above results, it has been suggested that the responsible bacteria are contained in the 9 bacterial strains.

[3 Bacterial Strains Isolated from Feces of Healthy Individuals Reduce Trypsin Activity in Mouse Feces]

Figure 9:
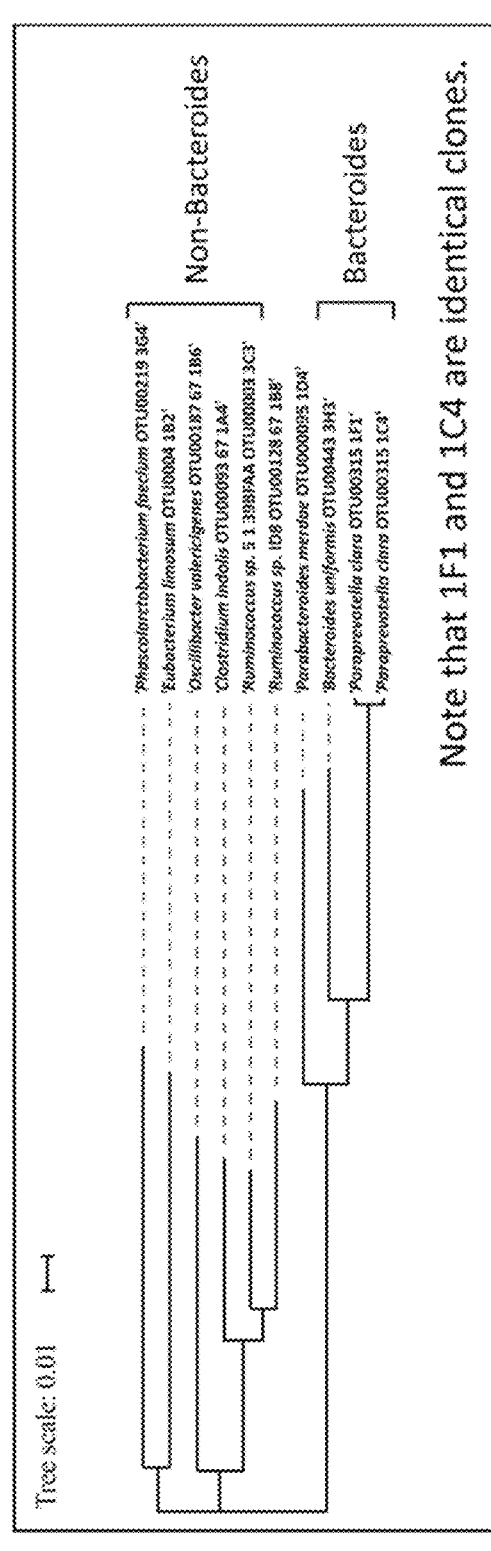
FIG. 9 shows a phylogenetic tree of the 9 bacterial strains observed to have a strong negative correlation in Spearman's correlation shown in FIG. 7. As shown in the figure, the 9 bacterial strains are divided into 3 bacterial strains belonging to the genus *Bacteroides* ("*Bacteroides*" in the figure) and 6 bacterial strains other than the genus *Bacteroides* ("Non-*Bacteroides*" in the figure).

As shown in FIG. 9, the above-mentioned 9 bacterial strains can be classified into a group containing 3 *Bacteroides* bacterial strains and 6 non-*Bacteroides* bacterial strains. Assuming that the function of reducing the activity of trypsin is systematically conserved, the responsible bacteria are considered to be contained in only one of the groups. In light of the above, in the same manner as in the above investigation, the former *Bacteroides*-inoculated group (hereinafter, 3-mix inoculation group) and the latter non-*Bacteroides*-inoculated group (hereinafter, 6-mix inoculation group) were evaluated.

As a result, as shown in FIG. 8, the fecal trypsin activity was significantly decreased in the 3-mix inoculation group, and was not decreased in the 6-mix inoculation group. From the above results, it has been suggested that the responsible bacteria were contained in the above 3 bacterial strains.

[*Paraprevotella clara* Isolated from Feces of Healthy Individuals Reduces Amount of Mouse Trypsin]

For the purpose of further narrowing down the responsible bacteria, trypsin and mono-cultured bacteria were made to coexist in vitro, and changes in the protein amount of trypsin were evaluated.

First, in an anaerobic chamber, His-tag-modified recombinant mouse trypsin and 9-mix, 6-mix, or 3-mix discussed above as a candidate for the responsible bacterium were co-cultured, and the amount of trypsin protein in the culture medium after 12 hours was evaluated.

As a result, although not shown in the figure, a decrease in trypsin was observed in the co-culture with 9-mix or 3-mix, but not in the co-culture with 6-mix. These results are in agreement with the results of the above-mentioned investigation of narrowing down the responsible bacteria in vivo. In other words, this in-vitro evaluation method is considered to be effective in further narrowing down the responsible bacteria. Additionally, the fact that the results of this in-vitro evaluation are in agreement with the results of the above-mentioned in-vivo evaluation suggests that the mechanism of the decrease in trypsin activity does not involve the host colon tissues, but only bacteria.

Figure 10:
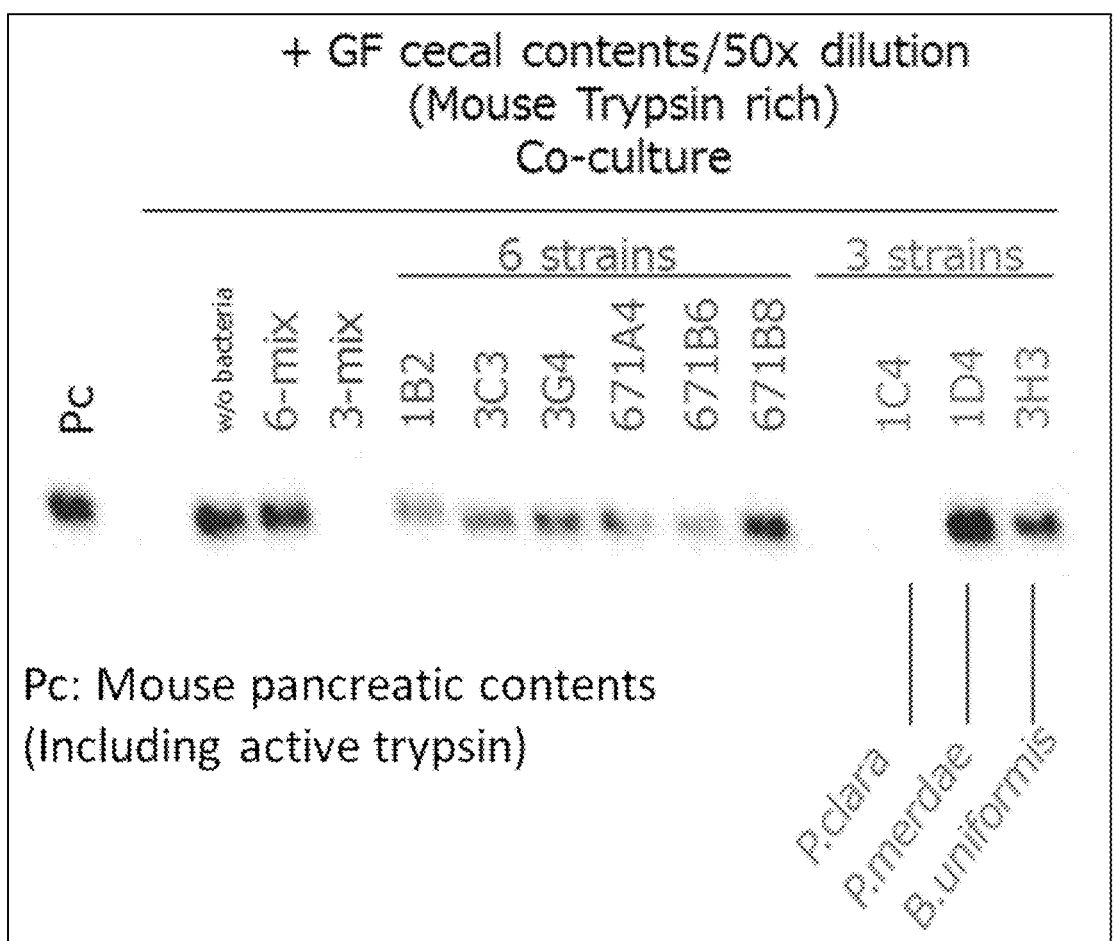
FIG. 10 is a photograph showing the results of evaluating the degradation of trypsin protein by isolated cultured bacteria. The cecal contents of GF mice containing trypsin and each bacterium were mixed and anaerobically cultured, and then the presence or absence of trypsin protein was evaluated by Western blotting. In the figure, "Pc" shows the results of evaluating the pancreatic contents of mice (including active trypsin), and "w/o bacteria" shows the results of evaluating the cecal contents of GF mice (unmixed with bacteria). The "6-mix" and "3-mix" show the results of evaluating the cecal contents of the mice mixed with the 6 bacterial strains and the 3 bacterial strains shown in FIGS. 8 and 9. The "6 strains" shows the results of evaluating the cecal contents of the mice mixed with the above 6 bacterial strains (1B2 to 671B8). The "3 strains" shows the results of evaluating the cecal contents of the mice mixed with the above 3 bacterial strains (1C4 to 3H3). Loss of trypsin protein was observed only in *P. clara* monobacterium, which is one of the constituent bacteria of 3mix and 3mix. That is, it is considered that the trypsin activity is suppressed by the degradation of trypsin by the bacteria *P. clara*.

Subsequently, each bacterium constituting 9-mix was co-cultured with trypsin for each monobacterium and evaluated in the same manner. As a result, as shown in FIG. 10, a decrease in the amount of trypsin protein was observed only when co-cultured with the *P. clara* 1C4 strain constituting 3-mix.

From the series of evaluation results, it has been found that the *P. clara* 1C4 strain derived from the feces of donor C is the responsible bacterium for reducing the amount of trypsin protein in mice.

[*Paraprevotella clara* Reduces Amount of Human Trypsin Protein]

As described above, it was demonstrated in vitro that the *P. clara* 1C4 strain isolated from the feces of a healthy individual reduces the amount of active trypsin in mice. Next, the above-mentioned in vitro experimental system was applied to human trypsin, and the effectiveness of its functions was verified. Specifically, in an anaerobic chamber, a mono-cultured *P. clara* 1C4 strain and recombinant human trypsin were co-cultured, and the amount of trypsin 12 hours later was evaluated by WB. As a result, although not shown in the figure, a decrease in the amount of human trypsin protein was observed only when co-cultured with the *P. clara* 1C4 strain. From the above results, it has been found that the *P. clara* 1C4 strain isolated from the feces of a healthy individual reduces the amount of human trypsin protein.

Example 3

[Inoculation of Bacterial Cocktail that Reduces Trypsin Activity Suppresses Inflammation of Colon Tissues]

Colitis model mice were used to examine the possibility of alleviating inflammation of the 3 bacterial strains identified (3-mix). For the colitis model mice, an IL10−/− enteritis onset model and a DSS induction model were selected. For the former, the model applied was one in which an IL10−/− mouse individual was made germ-free and then infected with *Enterobacter aerogenes* 11E12 strain, which was an enteritis-inducing bacterium isolated from the feces of a UC patient.

The 3-mix for reducing trypsin activity or 6-mix not involved in trypsin activity was orally inoculated into the stomach of the IL10−/−GF mouse, and 7 days later, a culture solution of *Enterobacter aerogenes* 11E12 strain monobacterium was similarly inoculated to induce colitis. The fecal trypsin activity was evaluated up to week 3 after inoculation. In addition, the degree of inflammation induced by week 3 after inoculation was evaluated by the fecal lipocalin level and the inflammation score based on histological observation of the large intestine.

Figure 11:
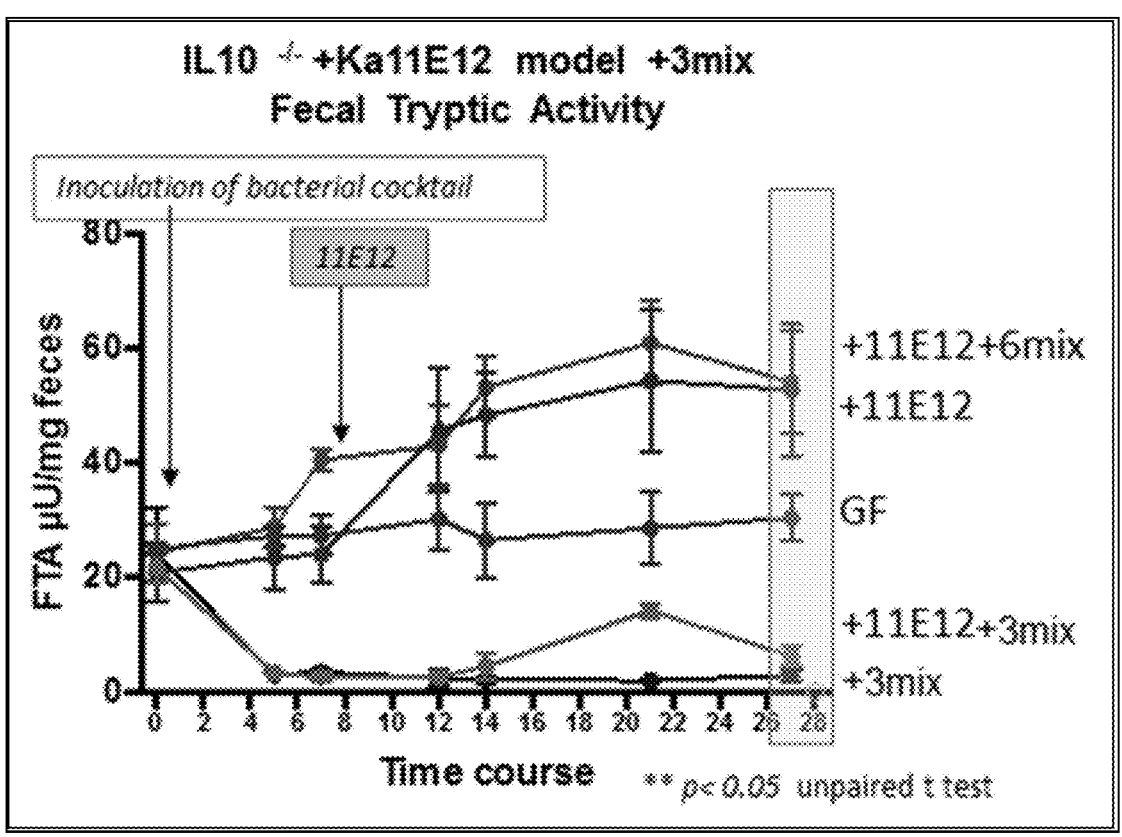
FIG. 11 is a graph showing the results of evaluating the suppression of the occurrence of ulcerative colitis (UC)-like inflammation due to the colonization of a trypsin activity-suppressing bacterial cocktail. IL10–/– mice were inoculated with the above-mentioned trypsin activity-suppressing bacteria 3mix or trypsin activity non-suppressing bacteria 6mix, and then infected with KaTTE12, which induces UC-like enteritis, and the mouse fecal trypsin activity was detected over time. In the figure, the horizontal axis shows the elapsed time since the inoculation of each bacterial cocktail. The vertical axis shows the fecal trypsin activity. The "11E12" shows the result of inoculation of only Ka11E12 to an IL10–/– mouse, and "11E12+6mix" and "11E12+3mix" show the results of inoculation of Ka11E12 to IL10–/– mice after inoculation of 3mix and 6mix. The "GF" shows the result of evaluating a germ-free mouse. The "3mix" shows the result of inoculation of only 3mix to an IL10–/– mouse.
Figure 12:
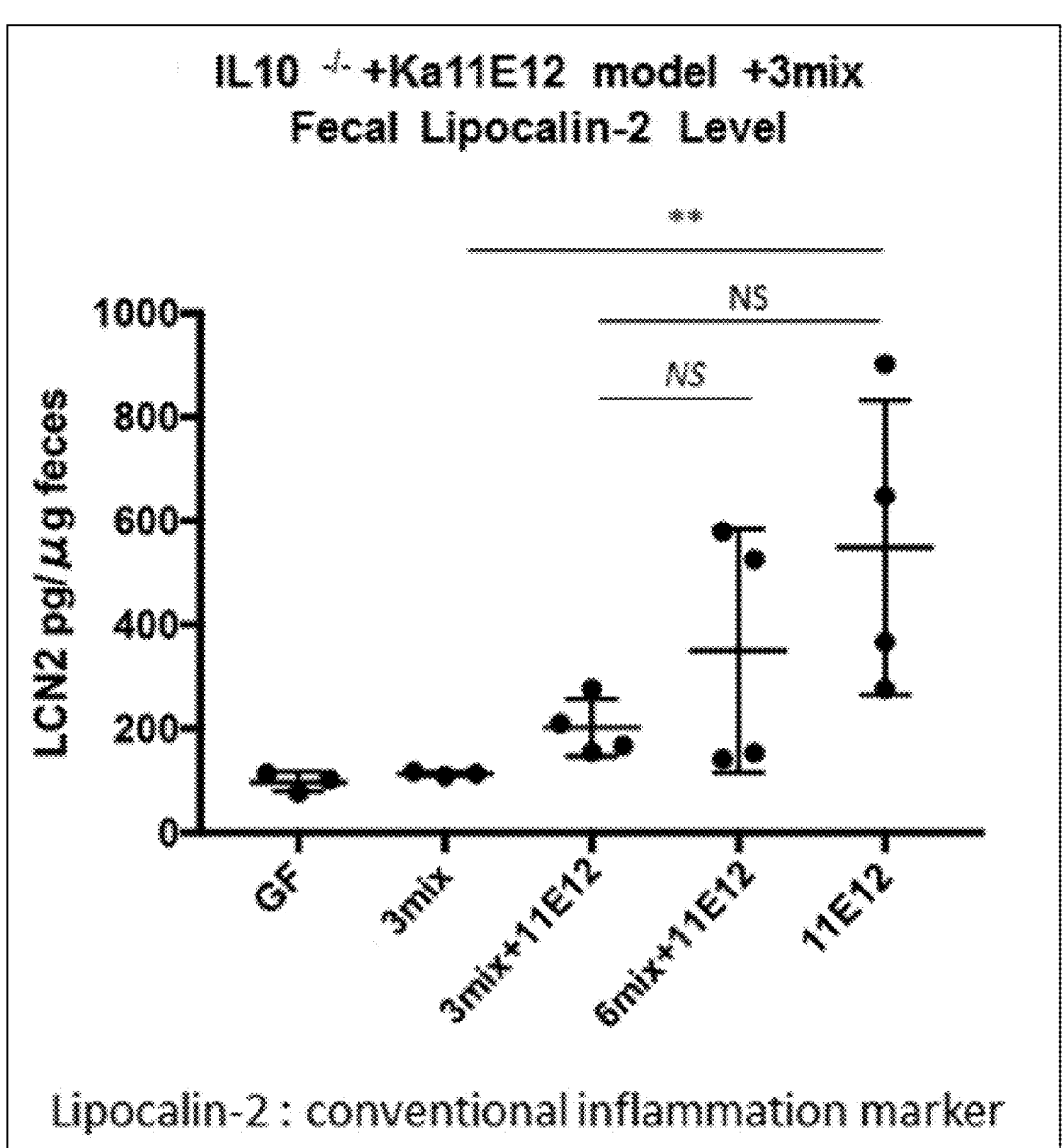
FIG. 12 is a dot plot diagram showing the results of evaluating the intestinal inflammation level 3 weeks after inoculation of Ka11E12 in the mice shown in FIG. 11. In the figure, the notation on the horizontal axis is the same as that in FIG. 11. The vertical axis shows the concentration of fecal inflammation markers (lipocalin-2, LCN2).

As a result, as shown in FIG. 11, high fecal trypsin activity was observed in the group inoculated with 11E12 strain and the group inoculated with 11E12 strain and 6-mix, while the trypsin activity was suppressed to a low level in the group inoculated with 11E12 strain and the 3-mix. In addition, as shown in FIG. 12, the fecal lipocalin level tended to be lower in the 3-mix inoculation group than in the 6-mix inoculation group. Further, although not shown in the figure, the histological inflammation score was also significantly lower.

A similar investigation was performed on DSS-induced model mice. GF mice were inoculated with 3-mix or 6-mix, and 14 days later, a 2.0% DSS aqueous solution was inoculated by free drinking for 7 days to induce colitis. The degree of inflammation induced by day 10 after DSS inoculation was evaluated by body weight variation, inflammation score based on histological observation of the large intestine, and expression level of inflammation markers. As a result, the rate of weight loss was lower in the 3-mix inoculation group than in the 6-mix inoculation group. In addition, the expression levels of inflammation marker genes including TNF-α and IL6 were also significantly low.

From the above investigation results, it has been found that the inoculation of 3-mix suppresses the inflammation of the colon tissues.

Example 4

[Genus *Paraprevotella* Reduces Trypsin Activity]

The preservability of the function of reducing trypsin activity observed in the *P. clara* 1C4 strain in related bacterial strains was evaluated.

For the *P. clara* JCM 14859$^T$ strain obtained from Japan Collection of Microorganisms, RIKEN BioResource Research Center (RIKEN BRC) and the *Paraprevotella xylaniphila* (*P. xylaniphila*) JCM 14860$^T$ strain corresponding to the other of the 2 species belonging to the genus *Paraprevotella* according to the phylogenetic tree classification as of November 2018, the ability to reduce trypsin activity in vitro was verified. A trypsin solution derived from the mouse cecal contents was mixed with a culture solution of each bacterium, incubated under anaerobic conditions for 12 hours, and then subjected to evaluation of the amount of active trypsin protein by WB.

Figure 13:
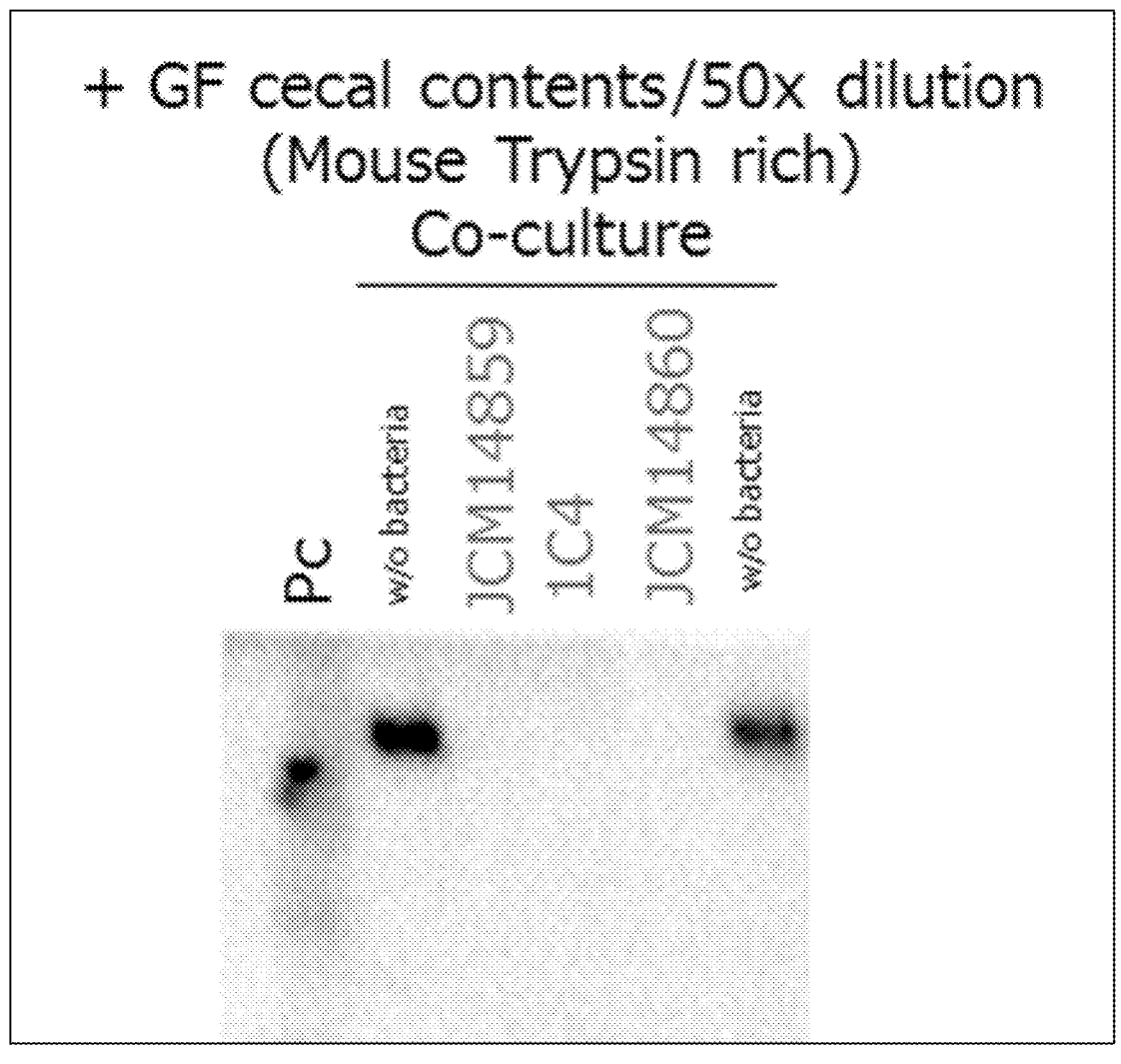
FIG. 13 is a photograph showing the results of evaluating the degradation of trypsin protein by *P. clara* and its related bacterial species. In the figure, "Pc" shows the results of evaluating the pancreatic contents of mice (including active trypsin), and "w/o bacteria" shows the results of evaluating the cecal contents of GF mice (unmixed with bacteria). The "1C4" shows the result of evaluating the cecal contents of a mouse mixed with the *P. clara* bacterial strain 1C4 (see FIG. 10) isolated in the present invention. The "JCM 14859" shows the result of evaluating the cecal contents of a mouse mixed with another strain of the bacteria *P. clara* different from 1C4. The "JCM 14860" shows the result of evaluating the cecal contents of a mouse mixed with the *P. xylaniphila* bacterial strain, which is a related species of the bacteria *P. clara*.

As a result, as shown in FIG. 13, the amount of trypsin protein was also below the detection limit of WB when mixed with any *Paraprevotella* strain.

From the above results, it has been found that all the bacterial species classified into the genus *Paraprevotella* in the phylogenetic tree classification as of November 2018 reduce the amount of active trypsin derived from mice.

Example 5

[Crosslink Test]

Figure 14:
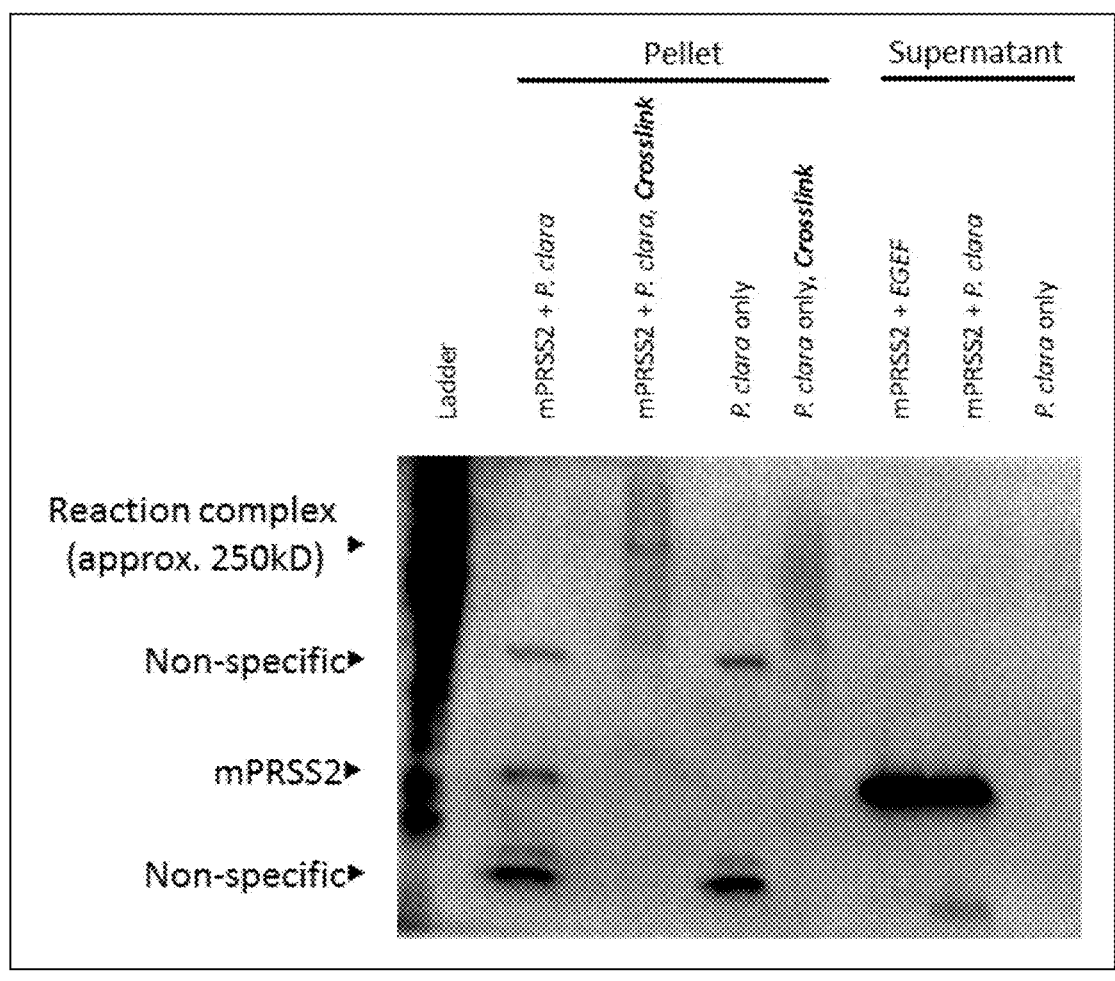
FIG. 14 is a photograph showing the results of a crosslink test between trypsin (mPRSS2) and a protein derived from the bacteria *P. clara*, analyzed by Western blotting using trypsin as a detection target. In the figure, "mPRSS2+*P. clara*" shows the result of analyzing the cell lysate of the bacteria *P. clara* simply incubated with mPRSS2, "mPRSS2+*P. clara* Crosslink" shows the result of analyzing the cell lysate of the bacteria *P. clara* incubated with mPRSS2 and further subjected to a crosslink reaction, "*P. clara*" shows the result of analyzing the cell lysate of *P. clara* without incubation with mPRSS2, and "*P. clara* Cross-link" shows the result of analyzing the cell lysate of *P. clara* not incubated with mPRSS2 but subjected to a crosslink reaction. The "mPRSS2+EGEF" shows the result of analyzing EGEF medium supplemented with mPRSS2, "mPRSS2+*P. clara*" shows the result of analyzing EGEF medium after incubating mPRSS2 and *P. clara*, and "*P. clara* only" shows the result of analyzing EGEF medium after incubating only *P. clara*. In the figure, "mPRSS2" shows the position of the band of mPRSS2 detected by Western blotting, and "Reaction complex (approx. 250 kDa)" shows the position of the band of the complex with the bacteria *P. clara*-derived protein (about 220 kDa) formed by adsorbing or binding to mPRSS2 (about 32 kDa). "Non-specific" shows the position of the non-specific band detected by Western blotting.

As shown in FIG. 14, a band was detected in the vicinity of 250 kDa only when mPRSS2 and the bacteria *P. clara* were mixed to form a crosslink by DSSO. Since this was not observed in the case of forming a crosslink without containing mPRSS2, it was presumed to be a complex protein composed of mPRSS2 and the constituent proteins of the bacteria *P. clara*. Considering that mPRSS2 is a protein of about 32 kDa, it is considered that trypsin is preferentially adsorbed or bound to a certain protein of about 220 kDa constituting the bacteria *P. clara*.

From these results, it is considered that the degradation phenomenon of trypsin protein is induced together with the phenomenon in which trypsin binds to a specific protein possessed by bacteria of the genus *Paraprevotella*.

[Trypsin Activity Inhibition Test]

Figure 15:
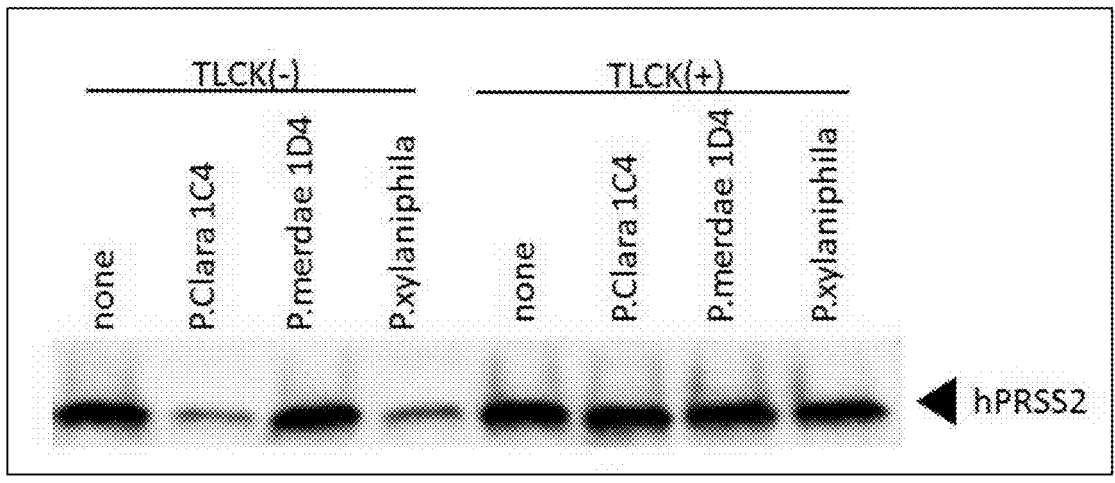
FIG. 15 is a photograph showing the results of a trypsin activity inhibition test. More specifically, it is a photograph showing the results of detecting hPRSS2 by Western blotting after incubating human PRSS2 (hPRSS2) treated with a trypsin activity inhibitor ("TLCK(+)" in the figure) or untreated hPRSS2 ("TLCK(−)" in the figure) and each of the bacteria (*P. clara* 1C4, *P. merdae* 1D4, or *P. xylaniphila*). Note that in the figure, "none" shows the result of incubating only trypsin in the absence of bacteria.

As shown in FIG. 15, when hPRSS2 unmodified with a TLCK inhibitor and bacteria of the genus *Paraprevotella* were mixed, the hPRSS2-derived band was thinned, and the degradation of hPRSS2 was induced. On the other hand, in the case of TLCK-hPRSS2 having modified TLCK to lose trypsin activity, the degradation of hPRSS2 was not induced. Considering that TLCK is an inhibitor of trypsin activity based on irreversible binding, it is considered that the degradation of trypsin by bacteria of the genus *Paraprevotella* is due to the promotion of trypsin autolysis.

From the results of the above [Crosslink Test] and [Trypsin Activity Inhibition Test], degradation of trypsin by bacteria of the genus *Paraprevotella* can be considered to be induced by binding the trypsin protein to a specific protein of the bacteria based on the effect of promoting trypsin autolysis.

INDUSTRIAL APPLICABILITY

As described above, according to the present invention, it is possible to suppress trypsin activity. Therefore, it is useful in treating and preventing diseases caused by trypsin activity (inflammatory bowel diseases such as ulcerative colitis and Crohn's disease).

ACCESSION NUMBER (1) Identification Label: 1C4
(2) Accession Number: NITE BP-02775
(3) Accession Date: Aug. 30, 2018
(4) Depository Institution: National Institute of Technology and Evaluation
(1) Identification Label: 1D4
(2) Accession Number: NITE BP-02776
(3) Accession Date: Aug. 30, 2018
(4) Depository Institution: National Institute of Technology and Evaluation
(1) Identification Label: 3H3
(2) Accession Number: NITE BP-02777
(3) Accession Date: Aug. 30, 2018
(4) Depository Institution: National Institute of Technology and Evaluation

---

The invention claimed is:

1. A method for suppressing intestinal trypsin activity in a target, said method comprising administering to said target a bacterium belonging to a genus *Paraprevotella*.

2. The method according to claim 1, wherein the bacterium belonging to the genus *Paraprevotella* is at least one bacterium selected from the group consisting of *Paraprevotella clara* and *Paraprevotella xylaniphila*.

3. The method according to claim 1, wherein the bacterium belonging to the genus *Paraprevotella* is at least one bacterium having a DNA composed of a DNA base sequence set forth in any of SEQ ID NOs: 1 to 3 or a DNA base sequence having at least 90% identity to the DNA base sequence.

4. The method according to claim 1, wherein the bacterium belonging to the genus *Paraprevotella* is at least one bacterial strain selected from the group consisting of a bacterial strain belonging to *Paraprevotella clara* specified by accession number NITE BP-02775, a *Paraprevotella clara* JCM 14859$^T$ strain, and a *Paraprevotella xylaniphila* JCM 14860$^T$ strain.

5. The method according to claim 1, further administering to said target at least one bacterium selected from the group consisting of *Parabacteroides merdae* and *Bacteroides uniformis*.

6. The method according to claim 5, wherein the *Parabacteroides merdae* is at least one bacterium having a DNA composed of a DNA base sequence set forth in SEQ ID NO: 4 or a base sequence having at least 90% identity to the DNA base sequence, and the *Bacteroides uniformis* is at least one bacterium having a DNA composed of a DNA base sequence set forth in SEQ ID NO: 5 or a DNA base sequence having at least 90% identity to the DNA base sequence.

7. The method according to claim 5, wherein the *Parabacteroides merdae* is a bacterial strain belonging to *Parabacteroides merdae* specified by accession number NITE BP-02776, and the *Bacteroides uniformis* is a bacterial strain belonging to *Bacteroides uniformis* specified by accession number NITE BP-02777.

\* \* \* \* \*